United States Patent [19]
Masamune et al.

[11] Patent Number: 6,025,350
[45] Date of Patent: Feb. 15, 2000

[54] C-4" SUBSTITUTED MACROLIDE ANTIBIOTICS

[75] Inventors: Hiroko Masamune, Noank; Wei-Guo Su, East Lyme; Bingwei V. Yang, Waterford, all of Conn.

[73] Assignee: Pfizer Inc., New York, N.Y.

[21] Appl. No.: 09/124,408

[22] Filed: Jul. 29, 1998

Related U.S. Application Data

[60] Provisional application No. 60/054,866, Aug. 6, 1997.

[51] Int. Cl.$^7$ .......................... A61K 31/395; A61K 31/33; C07D 267/00
[52] U.S. Cl. .......................... 514/183; 540/455; 540/457; 540/454; 549/266; 549/270
[58] Field of Search ..................... 540/454, 455, 540/457; 549/266, 270; 514/183

[56] References Cited

U.S. PATENT DOCUMENTS

| | | | |
|---|---|---|---|
| 4,740,502 | 4/1988 | Hannick et al. | 514/29 |
| 5,288,709 | 2/1994 | Freiberg et al. | 514/29 |

FOREIGN PATENT DOCUMENTS

| | | |
|---|---|---|
| 0126344 | 11/1984 | European Pat. Off. . |
| WO9742206 | 11/1997 | WIPO . |

OTHER PUBLICATIONS

Fernandes et al., "New Macrolides Active Against *Streptococcus pyogenes* With Inducible Or Constitutive Type Of Macrolide–Lincosamide–Streptogramin B Resistance," *Antimicrobial Agents and Chemotherapy*, 33(1), pp. 78–81 (1989).

Biedrzycki et al., "Erythromycin Derivatives. Part VI. Carbamates of Cyclic 11,12–Carbonate of Erythromycin A," *Polish J. Chemistry*, 52, pp. 315–319 (1978).

*Primary Examiner*—Johann Richter
*Assistant Examiner*—Taofiq A. Solola
*Attorney, Agent, or Firm*—Peter C. Richardson; Paul H. Ginsburg; Roy F. Waldron

[57] ABSTRACT

This invention relates to compounds of the formula

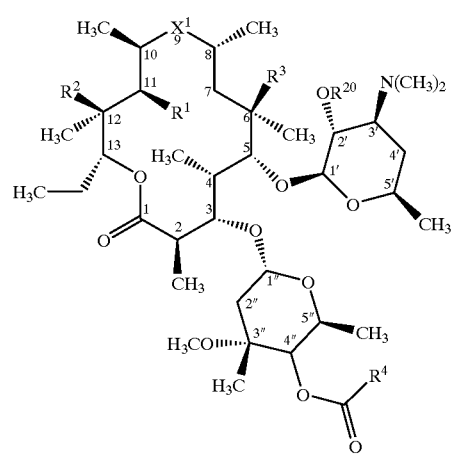

and to pharmaceutically acceptable salts thereof. The compounds of formula 1 are potent antibacterial and antiprotozoal agents that may be used to treat various bacterial and protozoal infections and disorders related to such infections. The invention also relates to pharmaceutical compositions containing the compounds of formula 1 and to methods of treating bacterial and protozoal infections by administering the compounds of formula 1.

10 Claims, No Drawings

C-4" SUBSTITUTED MACROLIDE ANTIBIOTICS

This applicaton claims benefit of provisional application Ser. No. 60/054866, filed Aug. 6, 1997.

BACKGROUND OF THE INVENTION

This invention relates to novel C-4" substituted macrolide derivatives that are useful as antibacterial and antiprotozoal agents in mammals, including man, as well as in fish and birds. This invention also relates to pharmaceutical compositions containing the novel compounds and to methods of treating bacterial and protozoal infections in mammals, fish and birds by administering the novel compounds to mammals, fish and birds requiring such treatment.

Macrolide antibiotics are known to be useful in the treatment of a broad sprectrum of bacterial and protozoal infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Like azithromycin and other macrolide antibiotics, the novel macrolide compounds of the present invention possess potent activity against various bacterial and protozoal infections as described below.

SUMMARY OF THE INVENTION

The present invention relates to compounds of the formula

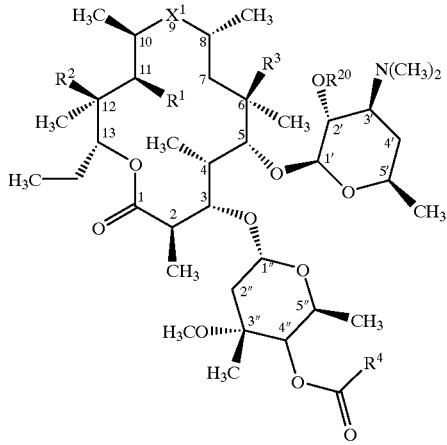

and to pharmaceutically acceptable salts thereof, wherein:

$X^1$ is —CH(—NR$^{18}$R$^{19}$)—, —C(O)—, —CH$_2$NR$^9$—, —NR$^9$CH$_2$—, or —C(=NR$^5$)—, wherein the first dash of each of the foregoing $X^1$ groups is attached to the C-10 carbon of the compound of formula 1 and the last dash of each group is attached to the C-8 carbon of the compound of formula 1;

$R^1$ and $R^2$ are each independently OH;

or $R^2$ is O and $R^1$ is $X^2$, and they are taken together as follows:

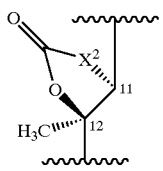

wherein $X^2$ is O, —N(R$^9$)—, or —N(NR$^9$R$^{10}$)—;

or $R^1$ is oxo, OH, or —NR$^9$R$^{10}$, $R^2$ is O and $X^1$ is —CH(—O)—, and $R^2$ and $X^1$ are taken together as follows:

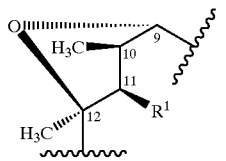

or $R^1$ is N, $R^2$ is O, $X^1$ is —C(=N)— or —CH(—NR$^9$)—, and $R^1$ is taken together with both $R^2$ and $X^1$ as follows:

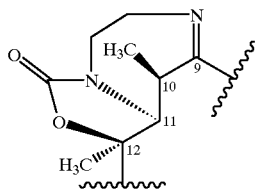

or

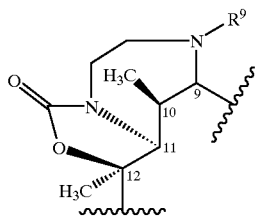

or $R^1$ is O and $X^1$ is —C(—NR$^9$)—, and they are taken together as follows:

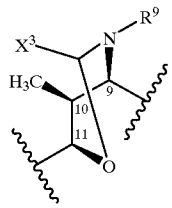

wherein $X^3$ is H, C$_1$–C$_6$ alkyl, or —(CH$_2$)$_m$O(C$_1$–C$_6$ alkyl) wherein m is an integer ranging from 1 to 4 and the alkyl moieties of the foregoing $X^3$ groups are optionally substituted by 1 or 2 substituents independently selected from halo, —NR$^9$R$^{10}$ and —OR$^9$;

$R^3$ is hydroxy or methoxy;

$R^4$ is —(CH$_2$)$_n$NR$^8$R$^{15}$ wherein n is an integer ranging from 0 to 6 and said $R^4$ group is optionally substituted by 1 to 3 R$^{16}$ groups, with the proviso that n is not 0 where R$^8$ is —C(O)(C$_1$–C$_{10}$ alkyl), —C(O)(CH$_2$)$_t$ ($C_6$–$C_{10}$ aryl), or —C(O)(CH$_2$)$_t$(4–10 membered heterocyclic);

$R^5$ is hydroxy, $C_1$–$C_6$ alkyl, $C_1$–$C_6$ alkoxy, —(CH$_2$)$_m$ ($C_6$–$C_{10}$ aryl), —(CH$_2$)$_m$(4–10 membered heterocyclic), or —(CH$_2$)$_m$O(CH$_2$)$_z$OR$^9$, wherein m is an integer ranging from 0 to 4 and z is an integer ranging from 1 to 6, and the foregoing $R^5$ groups, except hydroxy, are optionally substituted by 1 to 3 $R^{16}$ groups;

each $R^6$ and $R^7$ is independently H, —OR$^9$, $C_1$–$C_6$ alkyl, —(CH$_2$)$_m$($C_6$–$C_{10}$ aryl), or —(CH$_2$)$_m$(4–10 membered heterocyclic), wherein m is an integer ranging from 0 to 4, with the proviso that where $R^6$ and $R^7$ are both attached to the same nitrogen as —NR$^6$R$^7$, then $R^6$ and $R^7$ are not both —OR$^9$;

$R^8$ is $C_1$–$C_{10}$ alkyl, —C(O)($C_1$–$C_{10}$ alkyl), —(CH$_2$)$_q$CR$^{11}$R$^{12}$(CH$_2$)$_r$NR$^{13}$R$^{14}$ wherein q and r are each independently an integer ranging from 0 to 4 except that q and r are not both 0, —(CH$_2$)$_t$($C_6$–$C_{10}$ aryl), —(CH$_2$)$_t$(4–10 membered heterocyclic), —C(O)(CH$_2$)$_t$(C6–$C_{10}$ aryl), —(CH$_2$)$_j$(CH$_2$)$_t$($C_{6-C10}$ aryl), —C(O)(CH$_2$)$_t$(4–10 membered heterocyclic), —SO$_2$(CH$_2$)$_t$ ($C_6$–$C_{10}$ aryl), or —SO$_2$(CH$_2$)$_t$(4–10 membered heterocyclic), wherein j is an integer ranging from 0 to 2, t is an integer ranging from 0 to 5, the —(CH$_2$)$_t$— moieties of the foregoing $R^8$ groups optionally include a carbon-carbon double or triple bond where t is an integer between 2 and 5, and the foregoing $R^8$ groups are optionally substituted by 1 to 3 $R^{16}$ groups;

or $R^{15}$ and $R^8$ may be taken together with the nitrogen to which each is attached to form a 4–10 membered saturated monocyclic or polycyclic saturated ring or a 5–10 membered heteroaryl ring, wherein said saturated and heteroaryl rings optionally include 1 or 2 heteroatoms selected from O, S and —N(R$^6$)— in addition to the nitrogen to which $R^{15}$ and $R^8$ are attached, said —N(R$^6$)— is optionally =N— or —N= where $R^{15}$ and $R^8$ are taken together as said heteroaryl group, said saturated ring optionally may be partially unsaturated by including 1 or 2 carbon-carbon double bonds, and said saturated and heteroaryl rings, including the $R^6$ group of said —N(R$^6$)—, are optionally substituted by 1 to 3 $R^{16}$ groups;

or $R^{15}$ and $R^8$ may be taken together with the nitrogen to which each is attached to form a polycyclic moiety of the formula

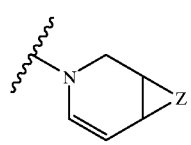

2

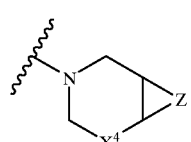

3 or

-continued

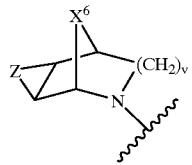

4 wherein V is 0 or 1, $X^4$ is —C(O)—, —CH(OH)—, —(CH$_2$)$_m$—, —N(R$^6$)(CH$_2$)$_m$—, —(CH$_2$)$_m$N(R$^6$)— or —(CH$_2$)$_m$O— wherein m is an integer ranging from 0 to 2, and $X^6$ is —(CH$_2$)$_w$— wherein w is 1 or 2, —CH$_2$O—, —OCH$_2$—, —CH$_2$N(R$^9$)—, or —N(R$^9$)CH$_2$—;

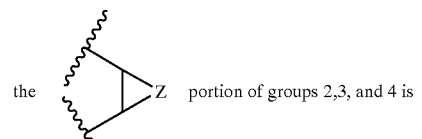

the Z portion of groups 2,3, and 4 is

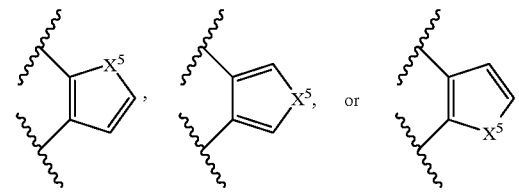

wherein $X^5$ is —CH=CH—, —S—, or —N(R$^6$)—, and the above groups of formulas 2 3 and 4, including the Z portions of said groups, are optionally substituted by 1 to 3 $R^{16}$ groups;

each $R^9$ and $R^{10}$ is independently H or $C_1$–$C_6$ alkyl;

each $R^{11}$, $R^{12}$, $R^{13}$ and $R^{14}$ is independently selected from H, $C_1$–$C_{10}$ alkyl, $C_1$–$C_{10}$ alkanoyl, —(CH$_2$)$_m$($C_{6-C10}$ aryl), —C(O)(CH$_2$)$_m$($C_6$–$C_{10}$ aryl), —(CH$_2$)$_m$(4–10 membered heterocyclic), and —C(O)(CH$_2$)$_m$(4–10 membered heterocyclic), wherein m is an integer ranging from 0 to 4, and wherein the foregoing $R^{11}$, $R^{12}$, $R^{13}$ and $R^{14}$ groups, except H, are optionally substituted by 1 to 3 $R^{16}$ groups;

or $R^{11}$ and $R^{13}$ are taken together to form —(CH$_2$)$_p$— wherein p is an integer ranging from 0 to 3 and r+p equals at least 2, such that a 4–9 membered saturated ring is formed that optionally may be partially unsaturated by including 1 or 2 carbon-carbon double bonds;

or $R^{13}$ and $R^{14}$ are taken together with the nitrogen to which each is attached to form a 4–10 membered monocyclic or polycyclic saturated ring or a 5–10 membered heteroaryl ring, wherein said saturated and heteroaryl rings optionally include 1 or 2 heteroatoms selected from O, S and —N(R$^6$)—, in addition to the nitrogen to which $R^{13}$ and $R^{14}$ are attached, said —N(R$^6$)— is optionally =N— or —N= where $R^{13}$ and $R^{14}$ are taken together as said heteroaryl group, said saturated ring optionally may be partially unsaturated by including 1 or 2 carbon-carbon double bonds, and said saturated and heteroaryl rings, including the $R^6$ group of said —N(R$^6$)—, are optionally substituted by 1 to 3 $R^{16}$ groups;

or $R^{13}$ and $R^{14}$ are taken together to form =C(—NR$^9$R$^6$)NR$^{10}$R$^7$;

or $R^{13}$ is H and $R^{14}$ is —C(=NR$^6$)NR$^9$R$^7$;

$R^{15}$ is H or $C_1$–$C_{10}$ alkyl, wherein the alkyl is optionally substituted by 1 to 3 $R^{16}$ groups;

each $R^{16}$ is independently selected from halo, cyano, nitro, trifluoromethyl, azido, —C(O)R$^{17}$, —C(O)OR$^{17}$, —OC(O)R$^{17}$, —OC(O)OR$^{17}$, —NR$^6$C(O)R$^7$, —C(O)NR$^6$R$^7$, —NR$^6$R$^7$, hydroxy, $C_1$–$C_6$ alkyl, —S(O)$_j$($C_{1-C6}$ alkyl) wherein j is an integer ranging from 0 to 2, $C_1$–$C_6$ alkoxy, —(CH$_2$)$_m$($C_6$–$C_{10}$ aryl), and —(CH$_2$)$_m$(5–10 membered heteroaryl), wherein m is an integer ranging from 0 to 4, said alkoxy group is optionally substituted by 1 to 3 groups selected from —NR$^9$R$^{10}$, halo, and —OR$^9$, and said aryl and heteroaryl subsituents are optionally substituted by 1 to 5 substituents independently selected from halo, cyano, nitro, trifluoromethyl, azido, —C(O)R$^{17}$, —C(O)OR$^{17}$, —CO(O)R$^{17}$, —OC(O)OR$^{17}$, —NR$^6$C(O)R$^7$, —C(O)NR$^6$R$^7$, —NR$^6$R$^7$, hydroxy, $C_1$–$C_6$ alkyl, and $C_1$–$C_6$ alkoxy;

each $R^{17}$ is independently selected from H, $C_1$–$C_{10}$ alkyl, —(CH$_2$)$_m$(C$_{6-C10}$ aryl), and —(CH$_2$)$_m$(4–10 membered heteroaryl), wherein m is an integer ranging from 0 to 4;

$R^{18}$ and $R^{19}$ are each independently selected from H, $C_1$–$C_6$ alkyl, —C(=NR$^5$)NR$^9$R$^{10}$, and —C(O)R$^9$, or $R^{18}$ and $R^{19}$ are taken together to form =CH(CR$^9$R$^{10}$)$_m$($C_6$–$C_{10}$ aryl), =CH(CR$^9$R$^{10}$)$_m$(4–10 membered heterocyclic), =CR$^9$R$^{10}$, or =C(R$^9$)C(O)OR$^9$, wherein m is an integer ranging from 0 to 4, and wherein the alkyl, aryl and heterocyclic moieties of the foregoing $R^{18}$ and $R^{19}$ groups are optionally substituted by 1 to 3 $R^{16}$ groups;

$R^{20}$ is H or —C(O)R$^9$.

More specific embodiments of this invention include compounds of formula 1 wherein $X^1$ is —CH(NH$_2$)—, $R^4$ is —(CH$_2$)$_n$NR$^8$R$^{15}$ wherein n is an integer ranging from 0 to 6, $R^{15}$ is H, ethyl or methyl, and $R^8$ is —(CH$_2$)$_q$CR$^{11}$R$^{12}$(CH$_2$)$_r$NR$^{13}$R$^{14}$ wherein q is 1 and r is 0, and $R^{11}$, $R^{12}$, $R^{13}$ and $R^{14}$ are as defined above.

Other specific embodiments of this invention include compounds of formula 1 wherein $X^1$ is —C(O)—, $R^1$ and $R^2$ are OH, $R^4$ is —(CH$_2$)$_n$NR$^8$R$^{15}$ wherein n is an integer ranging from 0 to 6, $R^{15}$ is H, ethyl or methyl, and $R^8$ is —(CH$_2$)$_q$CR$^{11}$R$^{12}$(CH$_2$)$_r$NR$^{13}$R$^{14}$ wherein q is 1 and r is 0, and $R^{11}$, $R^{12}$, $R^{13}$ and $R^{14}$ are as defined above.

Other specific embodiments of this invention include compounds of formula 1 wherein $X^1$ is —C(O)—, $R^4$ is —(CH$_2$)$_n$NR$^8$R$^{15}$ wherein n is an integer ranging from 0 to 6, $R^{15}$ is H, ethyl or methyl, $R^8$ is —(CH$_2$)$_q$CR$^{11}$R$^{12}$(CH$_2$)$_r$NR$^{13}$R$^{14}$ wherein q is 1 and r is 0, and $R^{11}$, $R^{12}$, $R^{13}$ and $R^{14}$ are as defined above; and $R^1$ is $X^2$ and $R^2$ is O, and they are taken together as follows:

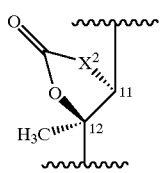

wherein $X^2$ is as defined above.

Other specific embodiments of this invention include compounds of formula 1 wherein $X^1$ is —N(CH$_3$)CH$_2$—, $R^1$ and $R^2$ are OH, $R^4$ is —(CH$_2$)$_n$NR$^8$R$^{15}$ wherein n is an integer ranging from 0 to 6, $R^{15}$ is H, ethyl or methyl, $R^8$ is —(CH$_2$)$_q$CR$^{11}$R$^{12}$(CH$_2$)$_r$NR$^{13}$R$^{14}$ wherein q is 1 and r is 0, and $R^{11}$, $R^{12}$, $R^{13}$ and $R^{14}$ are as defined above.

Other specific embodiments of this invention include compounds of formula 1 wherein $R^4$ is —(CH$_2$)$_r$NR$^8$R$^{15}$ wherein n is an integer ranging from 0 to 6, and $R^8$ and $R^{15}$ are taken together with the nitrogen to which each is attached to form a 4–10 membered saturated ring that optionally includes an additional heteroatom moiety selected from O, S, and —N((R$^6$)—, wherein said ring is optionally substituted by 1 to 3 $R^{16}$ groups.

Examples of preferred compounds of this invention include:

4"-O-[2-(N,N-bis-2,4,-dimethoxybenzyl)aminoethyl]aminocarbonyl-9deoxo-9-imino-11-deoxy-11-amino-9N, 11N-ethylene 6-O-methyl-erythromycin, 11,12-cyclic carbamate;

4"-O-[2-(N, N-bis-2,4-dimethoxybenzyl)aminoethyl aminocarbonyl erythromycylamine;

4"-O-[2-(N-3-methoxybutyl-N-2-methoxybenzyl) aminoethyl]aminocarbonyl erythromycylamine;

4"-O-[2-(N-2-methoxybenzyl)aminoethyl] aminocarbonyl-11-deoxy-11-amino 6-O-methyl-eythromycin, 11,12-cyclic carbamate;

4"-O-[2-(N-3-furylmethyl)aminoethyl]aminocarbonyl-11-deoxy-11-amino 6-O-methyl-erthromycin clarithromycin, 11,12-cyclic carbamate;

4"-O-[2-(N-3-methoxybutyl-N-α-methyl-2-methoxybenzyl)aminoethyl]aminocarbonyl erythromycylamine;

4"-O-{2-[2-(2-methoxyphenyl)-pyrrolin-1-yl] ethyl}aminocarbonyl erythromycylamine;

4"-O-[2-(N-2-tetrahydrofurylmethyl-N -α-methyl-2 methoxybenzyl)aminoethyl]aminocarbonyl erythromycylamine;

4"-O-[2-(N-tetrahydropyran-4-yl-N-2-methoxybenzyl) aminoethyl]aminocarbonyl erythromycylamine;

4"-O-{2-[N-(2-isopropyloxy)ethyl-N-2-methoxybenzyl] aminoethyl}aminocarbonyl erythromycylamine;

4"-O-{2-[N-(2-ethoxy)ethyl-N-2-methoxybenzyl] aminoethyl}aminocarbonyl erythromycylamine;

4"-O-[2-(N-ethyl-N-2-methoxybenzyl)aminoethyl] aminocarbonyl erythromycylamine;

4"-O-[2-(N-isopropyl-N-2-methoxybenzyl)aminoethyl] aminocarbonyl erythromycylamine;

4"-O-[2-(N-propyl-N-2-methoxybenzyl)aminoethyl] aminocarbonyl erythromycylamine;

4"-O-[2-(N-cyclopropylmethyl-N-2-methyoxybenzyl) aminoethyl]aminocarbonyl erythromycylamine;

4"-O-[2-(N-methyl-N-α-methyl-2-methoxybenzyl) aminoethyl]aminocarbonyl erythromycylamine;

4"-O-[2-(N-ethyl-N-α-methyl-2-methoxybenzyl) aminoethyl]aminocarbonyl erythromycylamine;

4"-O-[2-(N-propyl-N-α-methyl-2-methoxybenzyl) aminoethyl]aminocarbonyl erythromycylamine;

4"-O-[2-(N-α-methyl-2-methoxybenzyl)aminoethyl] aminocarbonyl azithromycin;

4"-O-[2-(N-isopropyl-N-2-methoxybenzyl)aminoethyl] aminocarbonyl erythromycylamine, methyl pyruvate imine;

4"-O-[2-(N-allyl-N-α-methyl-2-methoxybenzyl) aminoethyl]aminocarbonyl erythromycylamine;

4"-O-[2-(N-3-methoxybutyl-N-3-ethyl-5-methylisoxazol-4-ylmethyl)aminoethyl]aminocarbonyl 6-O-methyl-erythromycin;

4"-O-[2-(N-3-methoxybutyl-N-3,5-dimethylisoxazol-4-ylmethyl)aminoethyl]aminocarbonyl erythromycylamine;

4"-O-[2-(N-methyl-N-3,5-dimethylisoxazol-4-ylmethyl) aminoethyl]aminocartbonyl-11-deoxy-11-amino 6-O-methyl-erythromycin, 11,12-cyclic arbamate;

4"-O-[2-(N-methyl-N-3,5-dimethylisoxazol-4-ylmethyl) aminoethyl]aminocarbonyl 6-O-methyl-erthromycin;

4"-O-[2-(N-3,5dimethylisoxazol-4-ylmethyl)aminoethyl] aminocarbonyl 6-O-methyl-erythromycin;

4"-O-[2-(N-2-methoxybenzyl)aminoethyl] aminocarbonyl-11-deoxy-11-amino 6-O-methyl-erythromycin, 11,12-cyclic carbamate;

4"-O-[2-(N-α-butyl-2-methoxybenzyl)aminoethyl] aminocarbonyl-11-deoxy-11-amino 6-O-methyl-erythromycin, 11,12-cyclic carbamate;

4"-O-[2-(N-methyl-N-α-ethyl-2-methoxybenzyl) aminoethyl]aminocarbonyl azithromycin;

4"-O-[2-(N-2-methoxy-5-isopropylbenzyl)aminoethyl] aminocarbonyl-11-deoxy-11-amino 6-O-methyl-erythromycin, 11,12-cyclic carbamate;

4"-O-[4-(benzo[d]isoxazol-3-yl)-piperazin]carbonyl-11-deoxy-11-amino 6-O-methyl-erythromycin, 11,12-cyclic carbamate;

4"-O-[2-(N-chroman4-yl)aminoethyl]aminocarbonyl-11-deoxy-11-amino 6-O-methyl-erthromycin, 11,12-cyclic carbamate;

4"-O-[2-(N-propryl-N-α-methyl-2,4-dimethoxybenzyl) aminoethyl]aminocarbonyl erythromycylamine;

4"-O-[2-(N-ethyl-N-α-methyl-2-methoxybenzyl)amino] butyryl erythromycylamine;

4"-O-[2-(N-3-methoxybutyl-N-3-methoxypyridin-4-ylmethyl)aminoethyl]aminocarbonyl-6-O-methyl erythromycylamine;

4"-O-[2-(N-methyl-N-α-methyl-2,5-dichloro-thiophen-3-ylmethyl)aminoethyl]aminocarbonyl-6-O-methyl erythromycylamine;

4"-O-[2-(N-methyl-N-α-methyl-2,5-dimethyl-thiophen-3-ylmethyl)aminoethyl]aminocarbonyl-6-O-methyl erythromycylamine;

and the pharmaceutically acceptable salts of the foregoing compounds.

The invention also relates to a pharmaceutical composition for the treatment of a disorder selected from a bacterial infection, a protozoal infection, or disorder related to a bacterial infection or protozoal infection in a mammal, fish, or bird which comprises a therapeutically effective amount of a compound of formula 1, or a pharmaceutically acceptable salt thereof, and a pharmaceutically acceptable carrier.

The invention also relates to a method of treating a disorder selected from a bacterial infection, a protozoal infection, or disorder related to a bacterial infection or protozoal infection in a mammal, fish, or bird which comprises administering to said mammal, fish or bird a therapeutically effective amount of a compound of formula 1 or a pharmaceutically acceptable salt thereof.

The invention also relates to a pharmaceutical composition for the treatment of cancer, in particular non-small cell lung cancer, in a mammal, in particular a human, which comprises a therapeutically effective amount of a compound of formula 1, or a pharmaceutically acceptable salt thereof, and a pharmaceutically acceptable carrier.

The invention also relates to a method of treating cancer, in particular non-small cell lung cancer, in a mammal, which comprises administering to said mammal a therapeutically effective amount of a compound of formula 1 or a pharmaceutically acceptable salt thereof.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorder related to a bacterial infection or protozoal infection" include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, and glomerulonephritis related to infection by *Streptococcus pyogenes*, Groups C and G streptococci, *Clostridium diptheriae*, or *Actfnobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes , Streptococcus agalactiae*, Streptococcal groups C-F (minute-colony streptococci), viridans streptococci, *Corynebacterium minutissimum, Clostridium spp.*, or *Bartonella henselae*; uncomplicated acute urinary tract infections related to infection by *Staphylococcus saprophyticus* or *Enterococcus spp.*; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chiamydia trachomatis, Neisseria gonorrhoeae, S. aureus, S. pneumoniae, S. pyogenes, H. influenzae*, or *Listeria spp.*; disseminated *Mycobactetium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium spp.*; odontogenic infection related to infection by viridans streptococci; persistent cough related to infection by *Bordetella pertussis*; gas gangrene related to infection by *Clostridium perfringens* or *Bacteroides spp.*; and atherosclerosis or cardiovascular disease related to infection by *Helicobacter pylori* or *Chiamydia pneumoniae*. Bacterial infections and protozoal infections, and disorders related to such infections, which may be treated or prevented in animals include the following: bovine respiratory disease related to infection by *P. haemolytica, P. multocida, Mycoplasma bovis*, or *Bordetella spp.*; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae, Kiebsiella spp., Corynebacteiium*, or *Enterococcus spp.*; swine respiratory disease related to infection by *A. pleuro., P. multocida*, or *Mycoplasma spp.*; swine enteric disease related to infection by *E. coli, Lawsonia intracellularis, Salmonella*, or *Serpulina hyodysintenae*; cow footrot related to infection by *Fusobacterium spp.*; cow metritis related to infection by *E. coli*, cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*, skin and soft tissue infections in dogs and cats related to infection by *Staph. epidennidis, Staph. intermedius, coagulase neg. Staph.* or *P. multocida*; and dental or mouth infections in dogs and cats related to infection by *Alcaligenes spp., Bacteroides spp., Clostddium spp., Enterobacter spp., Eubacterium, Peptostreptococcus, Porphyromonas*, or

*Prevotella*. Other bacterial infections and protozoal infections, and disorders related to such infections, which may be treated or prevented in accord with the method of the present invention are referred to in J. P. Sanford et al., "The Sanford Guide To Antimicrobial Therapy," 26th Edition, (Antimicrobial Therapy, Inc., 1996).

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. Said alkyl group may include one or two double or triple bonds. It is understood that for cyclic moieties at least three carbon atoms are required in said alkyl group, and for said alkyl group to include a carbon-carbon double or triple bond at least two carbon atoms are required in said alkyl group. Where said alkyl moiety is defined as $C_1$–$C_{10}$ alkyl, this group includes $C_6$–$C_{10}$ bicyclo groups such as a bicyclo[3.1.1]heptylmethyl group.

The term "aryl", as used herein, unless otherwise indicated, includes an organic radical derived from an aromatic hydrocarbon by removal of one hydrogen, such as phenyl or naphthyl, as well as benzo-fused carbocyclic moieties such as 5,6,7,8-tetrahydro naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 5 membered heterocyclic group is thiazolyl, and an example of a 10 membered heterocyclic group is quinolinyl. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include chroman, benzodihydrofuran and benzimidazolyl.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include an amino moiety may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain compounds of the present invention may have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

The preparation of the compounds of the present invention is illustrated in the following Schemes. Unless otherwise indicated, in the following Schemes $R^1$ through $R^{20}$ and $X^1$ through $X^5$ are as defined above.

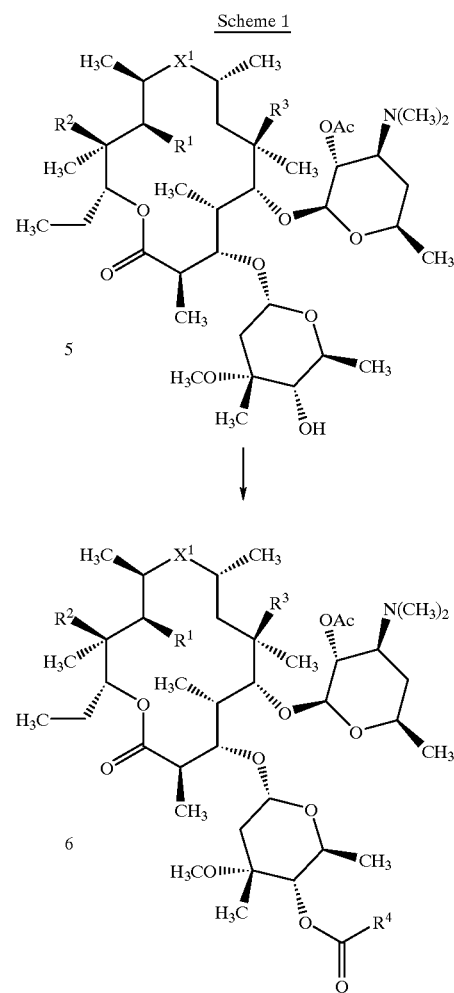

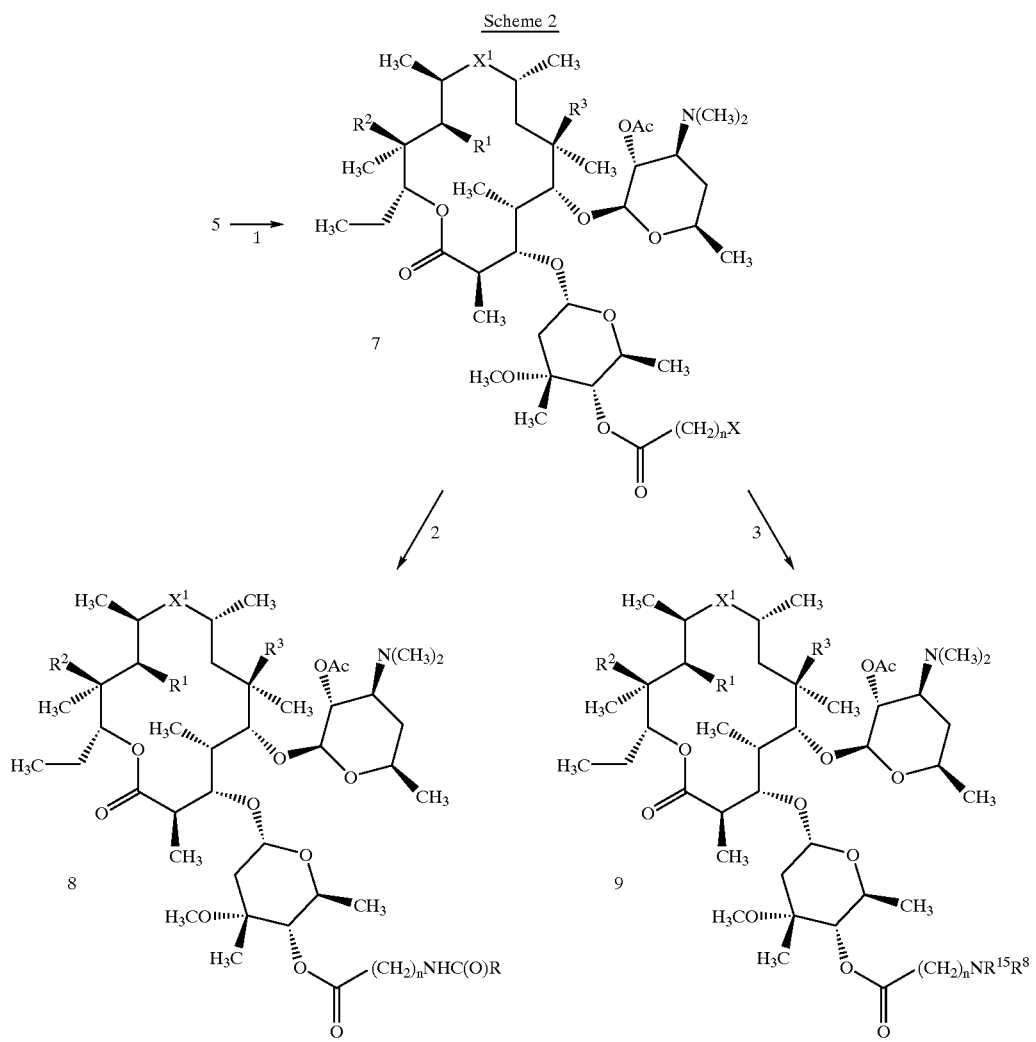

Scheme 3
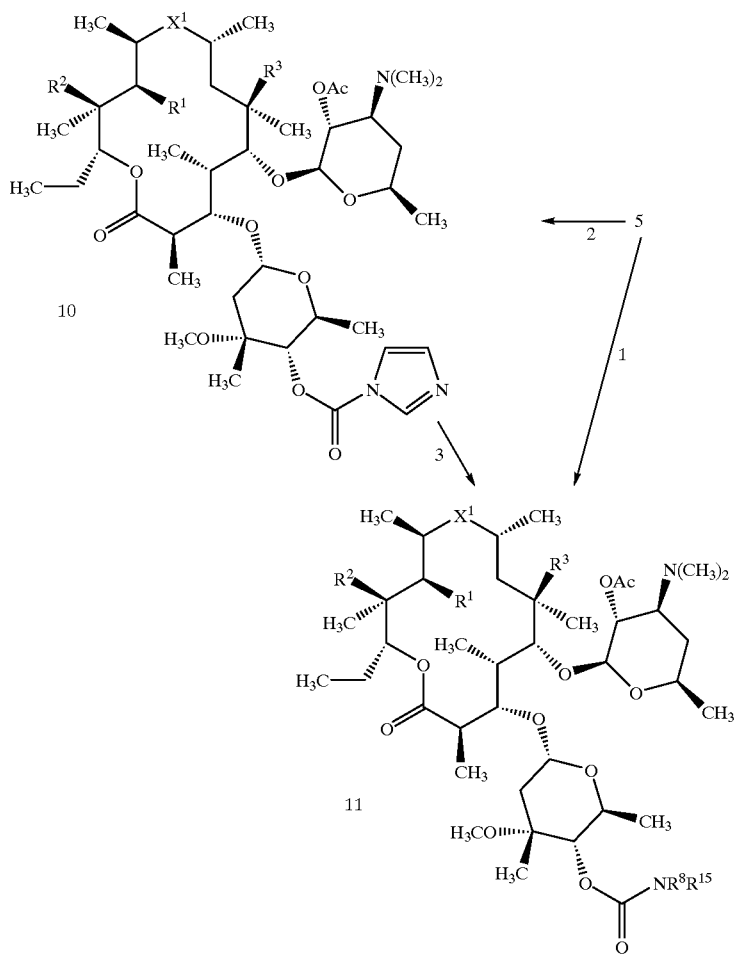

Scheme 4

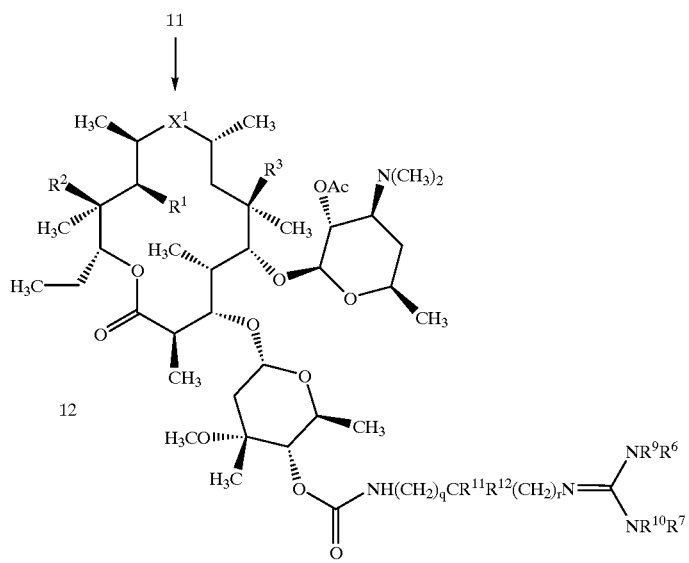

The sporeamicin A template may be prepared according to methods described in U.S. Pat. No. 5,288,709 and Freiberg et al., Bioorganic & Medicinal Letters, vol. 5, pages 1307–1310 (1995). The macrolide template designated M-8 in Table 2 below can be prepared according to methods described in Journal of Organic Chemistry 53, 2340 (1988). The macrolide template designated M-10 in Table 2 below can be prepared according to methods described in PCT international application publication number WO 92/09614 (published Jun. 11, 1992). The macrolide template designated M-1 1 in Table 2 below can be prepared according to methods described in Japanese patent application publication number 6-247996. The macrolide template designated M-14 in Table 2 below can be prepared according to methods described in Antimicrobial Agents Chemotherapy 35(6), 1116 (1991). All these starting materials require proper functional group protection before various modifications can take place, and deprotection after desired modifications are complete. The most commonly used protecting groups for amino moieties in the macrolide compounds of

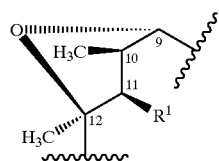

This invention uses a variety of macrolide templates as starting materials. They include azithromycin, erythromycin, clarithromycin, sporeamicin A, erythromycylamine as well as their analogs. Azithromycin can be prepared according to methods described in U.S. Pat. Nos. 4,474,768 and 4,517,359, referred to above. Erythromycin can be prepared, or isolated, according to methods described in U.S. Pat. Nos. 2,653,899 and 2,823,203. Clarithromycin can be prepared according to methods described in U.S. Pat. No. 4,331,803. The sporeamicin A template is the compound of formula 1 wherein $R^1$ is oxo, OH, or —$NR^9R^{10}$, $R^2$ is O and $X^1$ is —CH(—O)—, and $R^2$ and $X^1$ are taken together as follows:

this invention are benzyloxycarbonyl (Cbz) and t-butyloxycarbonyl (Boc) groups. Hydroxyl groups are generally protected as acetates or Cbz carbonates. The relative reactivity of various hydroxyl groups in the macrolide molecules of the general type claimed in this invention has been well established. Such differences in reactivity permit selective modification of different parts of the compounds of this invention.

To protect amino moieties, in particular the C-9 amino moiety of erythromycylamine, the macrolide is treated with t-butyl dicarbonate in anhydrous tetrahydrofuran (THF), or benzyloxycarbonyl N-hydroxysuccinimide ester (Cbz-OSu), to protect the C-9 amino group as its t-butyl or benzyl carbamate. Yields for this step are generally near quantitative. The Boc group is normally removed either by acid treatment or by following a two step procedure as follows:. (1) treatment with an excess amount (10 equivalents) of trimethylsilyl triflate in dichloromethane in the presence of 2,6-lutidine, and (2) desilylation with tetra-n-butylammonium fluoride in THF. The Cbz groups can be removed by conventional catalytic hydrogenation.

The C-2' hydroxyl group is a reactive hydroxyl group among the numerous hydroxyl groups present in macrolide compounds of the type claimed herein. The C-2' hydroxyl group is selectively protected by treating the compound with one equivalent of acetic anhydride in dichloromethane in the absence of external base. This process selectively converts the C-2' hydroxyl group into the corresponding acetate. The hydroxyl protecting group can be removed by treating the compound with methanol at a temperature ranging from about 0° C. to 40° C. to about 65° C. for 10 to 48 hours.

Alternatively, where the starting material for the preparation of the compounds of this invention is erythromycylamine, $N_{9a}$-desmethyl azithromycin or a macrolide corresponding to M-11 in Table 2 below (wherein $Y^1$ is H and a hydroxy group is attached at the C-4" carbon), these compounds can be treated with an excess of benzylchloroformate in THF/water at a pH of about 9 to provide N-9,2'-bis-Cbz protected erythromycylamine, $N_{9a}$-desmethyl azithromycin or M-11 macrolide (wherein a hydroxy group is attached at the C-4" carbon), in high yields. In this process, the amino group and the C-2' hydroxyl group can be protected in one step.

The C-2' protected macrolide derivatives will undergo selective acylation reactions at the C4" position, which is a means of introducing a variety of $R^4$ groups (wherein $R^4$ is as defined above). Other hydroxyl groups, such as those at the C-6, C-11 and C-12 positions, can generally be left unprotected. Acylation of the C-4" hydroxyl group offers a direct avenue to esters, carbonates and carbamates at the C4" position. The C-4" hydroxyl group can be selectively acylated to provide the corresponding esters using a variety of reagents, including carboxylic acids and a coupling agent such as 1,3-dicyclohexylcarbodiimide (DCC), carboxylic anhydrides, mixed anhydrides, chloroformates and acid chlorides. Acylation of the C-4" hydroxyl group is illustrated in Scheme 1 (wherein $R^4$ is as defined above) which illustrates the general reaction leading to the compounds of the present invention. The C-2' protected starting material in Scheme 1 (the compound of formula 5 (Ac is acetyl) is a useful starting material for the introduction of a variety of C-4" groups as described below.

With reference to step 1 of Scheme 2, acylation of the C-4" hydroxyl of the compound of formula 5 can be effected by treating the starting compound with about 1.0 equivalent of a compound of the formula $(X(CH_2)_nC(O))_2O$ (wherein X is chloro, bromo, or iodo, preferably chloro, and n is 1 to 6) in a solvent such as dichloromethane in the presence of pyridine at about 0° C. to provide the corresponding compound of formula 7 (wherein X is chloro, bromo or iodo and n is 1 to 6) in moderate yield. Displacement of the halo group with sodium azide in N,N-dimethylformamide (DMF) at about 0° C. to 80° C. for 3 to 12 hours converts X to $N_3$. Reduction of the azide, such as by catalytic hydrogenation, produces the corresponding amino ester (X is $NH_2$). The resulting primary amine can be converted into an alkylated secondary or tertiary amine, as shown in step 3 of Scheme 2, through reductive alkylation. Reductive alkylation of the C4" primary amine of the compound of formula 7 (X is —$NH_2$) with an aldehyde compound, such as a compound of the formula $R^8C(O)R^{15}$, wherein $R^{15}$ is H and $R^8$ is an alkyl group or substituted alkyl moiety, can be controlled to give either mono- or bis-alkylations, but alkylation with ketones generally yields only mono-alkylated products. For the preparation of symmetric bis-alkylamines, it is preferred to use an excess amount of an aldehyde and sodium triacetoxyborohydride or sodium cyanoborohydride in an inert solvent, such as dichloroethane or acetonitrile. The preferred method of controlling alkylation with an aldehyde to give a mono-alkylamine is through a two step sequence: (1) imine formation by reaction with an aldehyde in ethanol or acetonitrile and (2) reduction with sodium borohydride in methanol at about 0° C. Since the excess amount of aldehyde is reduced by sodium borohydride rapidly in methanol, the mono-alkylation is assured. This route is preferred for the synthesis of non-symmetric bis-alkylated products. Reacting the compound of formula 7 with a ketone in ethanol, followed by reduction with sodium borohydride in methanol, provides the mono-alkylated compound of formula 9 wherein $R^{15}$ is H and $R^8$ is an alkyl group or an analogous group. This compound can be further modified through reaction with an aldehyde as described above to provide the compound of the formula 9 wherein $R^{15}$ and $R^8$ are alkyl groups or analogous groups.

Primary amines on the C-4" substituent readily undergo acylation reactions under mild conditions. A variety of reagents can effect this transformation, including carboxylic acid anhydride, acid chloride, and carboxylic acid-DCC-DMAP combination (DMAP is 4-N,N-dimethylaminopyridine). These acylation reactions are selective for the primary amine. In general, acylation of the macrolide hydroxyl groups does not occur as long as the acylation reaction is carried out at an appropriate temperature and only one equivalent of acylating reagent is used. When the carboxylic acid-DCC-DMAP combination is employed, the acylation is completely specific for the amine. This method of acylation is therefore preferred. Thus, with reference to step 2 of Scheme 2, the compound of formula 7 may be treated with a carboxylic acid, such as a compound of the formula RC(O)OH (wherein R is $C_1$–$C_{10}$ alkyl, —$(CH_2)_qCR^{11}R^{12}(CH_2)_rNR^{13}R^{14}$ wherein q and r are each independently an integer ranging from 0 to 4 except that q and r are not both be 0, —$(CH_2)_t(C6$–$C_{10}$ aryl), —$(CH_2)_r$ (4–10 membered heterocyclic), or one of the foregoing groups that is substituted), in the presence of a coupling agent such as DCC to provide the compound of formula 8.

Alternatively, ester formation, as described above with reference to Scheme 2, can be effected using an activated carboxylic acid, such as a RCOOH/DCC/DMAP combination. For example, with reference to step 1 of Scheme 2, the compound of formula 5 can be acylated at the C4" position in good yields with 4-benzyloxycarbonylaminobutyric acid, DCC and DMAP at about 0° C. to 40° C. for a long period, such as several days, to provide the ester of formula 7 wherein n is 0 to 6 and X is —NHCbz. Removal of Cbz group by heterogeneous hydrogenolysis provides the compound of formula 7 wherein X is —$NH_2$. Conventional methods of effecting such hydrogenolysis are described in J. March, Advanced Organic Chemistry, (4th edition, 1992, J. Wiley & Sons), pages 771-780. Further modification of the primary amine according to methods described above provides substituted amine analogs of formulas 8 and 9, wherein Re and $R^{15}$ are as defined above.

Scheme 3 illustrates the preparation of compounds of the present invention that are C-4" carbamates. A variety of synthetic methods can be used to produce compounds of the present invention that are C-4 carbamates, including (1) reaction of a C-2' protected starting macrolide with an isocyanate and (2) reaction of a C-2' protected starting macrolide with N,N'-carbonyldiimidazole to form the acylimidazole intermediate which upon treatment with an amine leads to carbamate derivatives. With reference to step 1 of Scheme 3, the compound of formula 5 can be treated with an isocyanate of the formula $R^8NCO$ (wherein $R^8$ is as defined above) in dichloromethane in the presence of DMAP at about 0° C. for about 2 hours to provide the compound of formula 11 wherein $R^{15}$ is hydrogen.

With reference to step 2 of Scheme 3, the C-4 " acylimidazole derivative of formula 10 can be prepared by reacting the compound of formula 5 in toluene with N,N'-carbonyldiimidazole in the presence of anhydrous potassium carbonate at about 0° C. to 40° C. for about 24 hours. The C-4" acylimidazole of the formula 10 can be reacted with an amine of the formula $R^8R^{15}NH$ (wherein $R^8$ and $R^{15}$ are as defined above) in a solvent such as an acetonitrile-THF mixture at about 0° C. to 40° C. to provide the compound of the formula 11. Where, in the compound of formula 11, $R^8$ and $R^{15}$ are both H, this primary amine is a versatile moiety that is readily modified as described above.

Guanidino moieties can be introduced at a primary amine on the C4" substituent as illustrated in Scheme 4. In Scheme 4, the compound of formula 11, wherein $R^{15}$ is H and $R^8$ is —$(CH_2)_qCR^{11}R^{12}(CH_2)_rNH_2$, may be treated with a thiourea, such as a compound of the formula $R^6R^9NC(=S)NR^{10}R^7$ (wherein $R^9$, $R^{10}$, $R^6$ and $R^7$ are as defined above)

in a solvent such as DMF in the presence of mercuric chloride at ambient temperature (20°–25° C.). In this reaction, condensation takes place and the corresponding guanidine derivative of the formula 12 is formed. In addition, a substituted or unsubstituted thiazolyl group can be introduced at the C-4" primary amine by reacting the compound of the formula 11, wherein $R^{15}$ is H and $R^8$ is $-(CH_2)_qCR^{11}R^{12}(CH_2)_rNH_2$, according to the following sequence: (1) reacting said compound with N,N'-thiocarbonyldiimidazole followed by treatment with $NH_3(l)$ to give the corresponding thiourea, and (2) treating the thiourea with an α-halo ketone in ethanol at about 60° C.

Specific preparations that have been employed to prepare the intermediates described in the Schemes referred to above and the compounds of formula 1 are described below. In the following preparations, the abreviations Ac, Boc, Cbz, DCC, DMAP, THF and DMF are as defined above. The following abbreviations may also be used: TFA (trifluoroacetic acid), TMSOTf (trimethylsilyl trifluoromethanesulfonate), Et (ethyl), Me (methyl), iPrOH (isopropyl alcohol), and DBU (1,8-diazabicyclo[5.4.0]undec-7-ene).

PREPARATION 1

Preparation Of t-butyloxvcarbonyl-protected Macrolides

A macrolide, as described above, is dissolved in dry THF and to the mixture is added t-butyl dicarbonate (about 1.1 equivalents). The resulting mixture is stirred at about 0° C. to 40° C. for about 24 hours. All volatiles are removed on a rotovap. The residue is diluted with dichloromethane and washed with 5% aqueous sodium carbonate and brine. Drying over anhydrous potassium carbonate, fitration, evaporation of the filtrate and silica gel column chromatography (SGC) using 98:2:0.1/$CH_2Cl_2$—MeOH—conc. $NH_4OH$ gives the t-butyloxylcarbonyl-protected macrolide.

PREPARATION 2

Preparation of Benzyloxycarbonyl-protected Macrolide

A macrolide that includes an amino group, such as erythromycylamine, is dissolved in dry dichloromethane and to it is added benzyloxycarbonyl N-hydroxysuccinimde ester (about 1.1 equivalents). The resulting mixture is stirred at about 0° C. to 40° C. for about 12 hours before 5% sodium carbonate is introduced. Phases were separated and the aqeous phase extracted with dichloromethane. The combined organics were washed with brine, dried over potassium carbonate, filtered, concentrated and purified by SGC using 98:2:0.1/$CH_2Cl_2$—MeOH-conc. $NH_4OH$ to provide the benzyloxycarbonyl-protected macrolide.

PREPARATION 3

Removal of Boc Protecting Group

A macrolide that includes a Boc-protected amino group is dissolved in dry dichloromethane and cooled to about −10° C. 2,6-lutidine (15 equivalents) and trimethylsilyl triflate (10 equivalents) are added to the mixture. The resulting mixture is stirred at about −10° C. to about 0° C. for about 2 hours before it is poured into 5% sodium carbonate. Extraction with dichloromethane, drying over potassium carbonate, filtration and concentration of the filtrate provides the crude silyl ether which is used in the next step.

The above obtained crude material is dissolved in THF and treated with a 1N solution of tetrabutylammonium fluoride in THF (15 equivalents). The resulting solution is stirred at about 0° C. to 40° C. for about 24 hours. THF is removed in vacuo and the residual oil is dissolved in dichloromethane and washed with 5% sodium carbonate. Drying over potassium carbonate, filtration, concentration of the filtrate and SGC using an appropriate solvent system ($CH_2Cl_2$—MeOH-conc $NH_4OH$) provides the macrolide with the Boc protecting group removed.

PREPARATION 4

Removal of Cbz Protecting Group

A macrolide that includes a Cbz-protected hydroxy or amino group is dissolved in methanol. A palladium catalyst (10% Pd on carbon, 20% wtw) is added to the mixture. The mixture is hydrogenated on a Parr shaker for about 2 hours. Filtration through Celite™, concentration and SGC purification ($CH_2Cl_2$—MeOH—conc $NH_4OH$) produces the macrolide with the Cbz protecting group removed.

PREPARATION 5

Acetylation of the 2'-Hydroxyl Group

A macrolide, as described above, is dissolved in dry dichloromethane and treated with acetic anhydride (about 1 equivalent). The resulting mixture is stirred at about 0° C. to 40° C. for about 18 hours. Water is added and the pH is adjusted to 10 with 1N sodium hydroxide solution. After stirring for 15 minutes, the layers are separated and the aqueous layer is extracted with dichloromethane. The combined extracts are washed with saturated sodium chloride solution and dried over anhydrous potassium carbonate. Filtration and concentration of the filtrate provides the macrolide which includes the C-2'-acetate.

PREPARATION 6

Deacetylation of the 2'-acetate

The above macrolide that includes the C-2'-acetate is dissolved in methanol and left standing for about 3 days. Concentration to dryness yields the deacetylated macrolide.

PREPARATION 7

Introduction of Bis-Cbz Protecting Groups

A macrolide, such as erythromycylamine, $N_{9a}$-desmethyl azithromycin or a macrolide corresponding to template M-11 in Table 2 below (wherein $Y^1$ is H and a hydroxy groups is attached at the C-4" carbon), is dissolved in THF. The solution is cooled to about 020 C. Cbz-Cl (5 equivalents) and 1 N sodium hydoxide are added to the mixture at the same time via addition funnels to maintain the pH of the solution at 9. After the addition is completed, the reaction mixture is stirred at about 0° C. to 40° C. for an additional 3 hours during which 1N sodium hydroxide is added to maintain the pH at 9. The reaction mixture is diluted with 5% sodium carbonate and extracted with ethyl acetate. The combined extracts are washed with brine, dried over $MgSO_4$, filtered, concentrated in vacuo, and purified by SGC using 98:2:0.001/$CH_2Cl_2$—MeOH—conc $NH_4OH$ to provided the bis-Cbz protected macrolide, such as 9,2'-bis-Cbz-erythromycylamine.

PREPARATION 8

Preparation of C4" Esters by Reaction with Anhydrides

A macrolide, such as the above intermediate compound of formula 5, is dissolved in dry dichloromethane and the mixture is cooled to about 0° C. Pyridine (about 1.2 equivalents) and a carboxylic acid anhydride (about 1.1 equivalents) are added to the mixture. The reaction mixture is allowed to warm to about 20° C. to 40° C. and stirred for about 24 hours. The mixture is poured into 5% sodium carbonate and extracted with dichloromethane. The combined extracts are washed with brine, dried over potassium carbonate, filtered, concentrated and purified by SGC using 98:2:0.1/$CH_2Cl_2$—MeOH—conc $NH_4OH$ to produce the C-4" ester.

PREPARATION 9

Preparation of C4" Esters by Coupling with Carboxylic Acids

A macrolide, such as the above intermediate compound of formula 5, is dissolved in dry dichloromethane. A carboxylic acid (2 equivalents), DCC (2 equivalents) and DMAP (0.5 equivalents) are added to the mixture. The resulting mixture is stirred at about 0° C. to 40° C. for about 3 days. Workup as described above provides the C-4" ester of the starting macrolide.

PREPARATION 10

Preparation of C-4" carbamates from Isocyanates

A macrolide, such as the above intermediate compound of formula 5, is dissolved in dichloromethane and treated with DMAP (0.5 equivalent) and an isocyanate of the formula $R^8NCO$ (about 1.0 equivalent), wherein $R^8$ is as defined above, at a temperature within the range of about 0° C. to 23° C. The reaction is usually complete within 2 to 6 hours. The reaction mixture is worked up as described above and the product is purified by SGC using 2 to 5% MeOH in $CH_2Cl_2$ containing 0.1% $NH_4OH$ to give the C4" carbamate.

PREPARATION 11

Preparation of C-4" Carbamates via an Acylimidazole Intermediate

A C-2' protected macrolide, such as the above compound of formula 5, is dissolved in dry toluene. Anhydrous potassium carbonate (3 equivalents) and N,N'-carbonyldiimidazole (1.05 equivalents) are added to the reaction mixture. The resulting mixture is stirred at a temperature of about 0° C. to 40° C. for about 24 hours. The reaction mixture is then poured into 5% sodium carbonate and extracted with ethyl acetate (3×40 ml). The combined extracts are washed with brine, dried over magnesium sulfate, filtered and concentrated to afford the corresponding C-4" acylimidazole which is used without purificiafion.

The C-4" acylimidazole obtained as described above is dissolved in THF or THF/$CH_3CN$ (1:4). An amine of the formula $R^8R^{15}NH$ (about 1–2 equivalents), wherein $R^8$ and $R^{15}$ are as defined above. The reaction mixture is stirred at a temperature within the range of about 0° C. to 65° C. for a period of about 12 to 96 hours until the reaction is complete. The solvent is removed in vacuo and the residual solid is resuspended into dichloromethane and washed with 5% sodium chloride and brine. Drying over potassium carbonate, filtration, concentration of the filtrate and purification by SGC using 2 to 8% methanol-dichloromethane containing 0.1 to 0.5% concentrated ammonia provides the corresponding C-4" carbamate.

PREPARATION 12

Mono-substitution of C4" Side Chain Primary Amine

A compound of formula 1 wherein $R^4$ includes a primary or secondary amine is dissolved in dry ethanol or acetonitrile. A ketone of the formula RC(O)R (about 1.2 equivalents) or an aldehyde of the formula RC(O)H (about 1.2 equivalents), wherein R corresponds to the above substituents $R^8$, $R^{13}$ or $R^{15}$. The solution is stirred at a temperature ranging from about 23° C. to 80° C. for a period of about 12 to 72 hours. The solvent is removed in vacuo to yield the corresponding imine.

The crude imine obtained as described above is dissolved in methanol and cooled to about 0° C., and sodium borohydride (about 1.0 equivalent) is added to the mixture. The resulting mixture is stirred at about 0° C. for about 1 to 3 hours. Water is added and pH is adjusted to 3 with 1N HCl. After stirring at about 0° C. to 40° C. for about 15 minutes, the mixture is poured into 5% sodium carbonate and extracted with dichloromethane. The combined extracts are washed with saturated sodium chloride, dried over potassium carbonate and filtered. Concentration of the filtrate and SGC purification using 2 to 5% methanol-dichloromethane containing 0.2 to 0.4% concentrated ammonia provide the corresponding compound of formula 1 wherein the primary or secondary amine is substituted by R.

PREPARATION 13

Substitution of C-4" Side Chain Primary or Secondary Amines

A compound of formula 1 wherein $R^4$ includes a primary or secondary amine is dissolved in an appropriate solvent, such as $CH_2Cl_2$, 1,2-dichloroethane or acetonitrile. An aldehyde of the formula RC(O)H (about 1.0 equivalent), wherein R corresponds to the above substituents $R^8$, $R^{13}$ or $R^{15}$, sodium triacetoxyborohydride (about 1.2 equivalents) and sodium acetate (about 1.2 equivalents) are added to the mixture. The resulting mixture is stirred at about 0° C. to 40° C. for about 12 to 72 hours. Solvent is removed by a stream of air. The residual solid was resuspended into methanol and water. The pH is adjusted to 3 with 1N HCl and the resulting mixture is stirred for about 15 minutes. The mixture is poured into 5% sodium carbonate and extracted with dichloromethane. Drying over potassium carbonate, filtration, concentration and SGC using an appropriate solvent system provides corresponding reductive amination product.

PREPARATION 14

Preparation of Amides

A compound of formula 1 wherein $R^4$ includes a primary or secondary amine is dissolved in dichloromethane. DMAP (0.5 equivalent), a carboxylic acid (1.1 equivalents) and DCC (1.1 equivalents) are added to the mixture. The resulting mixture is stirred at 0° C. to 40° C. for about 4 to 24 hours. The mixture is poured into 5% sodium carbonate and extracted with dichloromethane. The combined extracts are washed with brine, dried over potassium carbonate, filtered, concentrated and purified by SGC using 2 to 5% methanol-dichloromethane containing 0.1 to 0.3% concentrated ammonia to provide the corresponding amide.

PREPARATION 15

Preparation of Guanidines

A compound of formula 1 wherein $R^4$ includes a primary amine and a N,N'-diarythiourea (1.0 equivalent) are dissolved in DMF. Mercuric chloride (1.0 equivalent) is added to the mixture, and the mixture is then stirred at about 0° C. to 40° C. for about 2 to 12 hours. The reaction mixture is diluted with ethyl acetate and stirred for about 20 minutes. The solids are filtered off through Celite™. The filtrate is washed with 5% sodium carbonate, brine, and dried over potassium carbonate. Filtration, concentration and SGC purification using 2 to 8% methanol-dichloromethane containing 0.2 to 0.5% concentrated ammonia provide the corresponding tri-substituted guanidine derivative.

The following preparation describe the preparation and incorporation of various cyclic $R^8$ and $R^{15}$ groups into the compounds of formula 1.

PREPARATION 16

5-Hydroxyl-5-(2-methoxyphenyl)-1-pentene

To a solution of 3-butenylmagnesium bromide in THF (0.50 M, 200 mL) at 0° C. was added o-anisaldehyde (13.62 g, 100 mmol) in THF (20 mL) dropwise and the reaction mixture was heated under reflux for 1 hour. Water was added, the aqueous layer was extracted with ether (x4), and the combined organic layers were washed with brine, dried over $MgSO_4$ and evaporated in vacuo to give the title compound. The crude product was used for Preparation 17 without purification. $^1H$ NMR (CDCl$_3$, 400 MHz) δ: 7.3 (2H), 6.9 (2H), 5.8 (2H), 4.8–5.1 (3H), 3.85 (3H, OMe), 2.5 (1 H), 1.8–2.3 (4H).

PREPARATION 17

5-Azido-5-(2-methoxyphenyl)-1-pentene

To a solution of crude 5-hydroxyl-5-(2-methoxyphenyl)-1-pentene, prepared as described above, in toluene (150 mL) at 0° to 40° C. was added diphenylphosphoryl azide (25.86 mL, 120 mmol) followed by DBU (17.95 mL, 120 mmol) and the resulting reaction mixture was stirred at room temperature (20° C. to 25° C.) for 28 hours. $H_2O$ was added, the aqueous layer was extracted with ether (x4), and the combined organic layers were washed with $H_2O$ (x2), 0.5N HCl (x2) and brine (x2), dried over $MgSO_4$ and evaporated in vacuao. The crude product was purified by silica gel flash chromatography (5% EtOAc-95% hexanes) to provide the title compound as a colorless liquid (14 g). $^1H$ NMR (CDCl$_3$, 400 MHz) δ: 6.8–7.4 (4H), 5.8 (1H) (2H), 3.83 (3H, OMe), 1.8–2.2 (4H), 5.0

PREPARATION 18

5-Amino-5-(2-methoxyphenyl)-1-pentene

To a solution of 5-azido-5-(2-methoxyphenyl)-1-pentene (1.59 g. 7.33 mmol) in anhydrous ether (10 mL) at 0° C. was added to LiAlH$_4$ in diethyl ether (1.OM, 7.33 mL) dropwise over a period of 20 minutes. The ice bath was removed and the reaction mixture was kept at room temperature for 25 minutes. The reaction solution was cooled to 0° C. to 40° C. and saturated $Na_2SO_4$ solution was added dropwise until no hydrogen gas was evolved. Anhydrous $Na_2SO_4$ was added followed by diethyl ether (70 mL), the resulting suspension was stirred at room temperature for 1 hour and the solution was then filtered through a pad of Celite™. The filtrate was evaporated to give the title compound (1.63 g) as a colorless oil, which was used for the Preparation 19 without purification. $^1H$ NMR (CDCl$_3$, 400 MHz)δ: 7.22 (2H), 6.93 (3H), 5.80 (1H), 4.92 (2H), 4.13 (1H), 3.82 (3H, OMe), 1.2–2.2 (6H).

PREPARATION 19

5-(N-(carbobenzyloxy)amino)-5-(2-methoxyphenyl)-1-pentene

To a solution of crude 5-amino-5-(2-methoxyphenyl)-1-pentene (1.63 g) in $CH_2Cl_2$ (10 mL) at 0° C. was added DMAP (1.15 g, 9.38 mmol) followed by Cbz-Cl (1.34 mL, 9.38 mmol) and the resulting solution was stirred at room temperature overnight. Ether was added, the aqueous layer was extracted with diethyl ether (x4), and the combined organic layers was washed with brine, dried over $MgSO_4$ and evaporated in vacuo. The crude product was purified by silica gel flash chromatography (5% EtOAc-95% hexanes) to provide the title compound as a white solid (1.84 g). $^1H$ NMR (CDCl$_3$, 400 MHz) δ: 3.82 (3H, s, OMe), 2.0 (4H, m).

PREPARATION 20

2-Hydroxymethyl-5-(2-methoxyphenyl)-N-(carbobenzyloxy)-tetrahvdropyrrole

To a solution of 5-(N-(carbobenzyloxy)amino)-5-(2-methoxyphenyl)-1-pentene (1.84 g) in THF (103 mL) at room temperature was added $Hg(OAc)_2$. The resulting solution was stirred at room temperature overnight. Saturated $NaHCO_3$ (80 mL) was added over a period of 15 minutes, the resulting yellow solution was stirred at room temperature for 40 minutes, and a saturated solution of 4.1 g KBr was added. The resulting white suspension was stirred at room temperature for 2 hours. The two layers were separated, the aqueous layer was extracted with ether, and the combined organic layers were washed with brine, dried over $MgSO_4$ and evaporated in vacuo. The crude product was purified by silica gel flash chromatography (5% EtOAc-95% hexanes) to provide 2-(bromomercurio)methyl-5-(2-methoxyphenyl)-1-(N-(carbobenzyloxy)amino)-tetrahydropyrrole (3.7 g).

Oxygen gas was bubbled into a suspension of $NaBH_4$ (289 mg, 9.09 mmol) in DMF (250 mL) at room temperature for 1 hour. A solution of 2-(bromomercurio)methyl-5-(2-methoxyphenyl)-1-(N-carbobenzyloxy)amino)-tetrahydropyrrole (3.7 g) in DMF (76 mL) was added dropwise over 2 hours with continuous introduction of oxygen. The bubbling of oxygen into the mixture was continued for another hour. The reaction mixture was filtered through Celite™, and the filtrate was evaporated in vacuo to give a residue, which was purified by silica gel flash chromatography (5% EtOAc-95% hexanes) to provide the title compound as a colorless oil. $^1H$ NMR (CDCl$_3$, 400 MHz) δ: 3.78 (3H, s, OMe), 5.00 (1H, d, J=12.8 Hz, AB), 4.94 (1H, d, J=12.8 Hz, AB).

PREPARATION 21

2-Methoxymethyl-5-(2-methoxyphenyl)-N-(carbobenzyloxy)-tetrahydropyrrole

To a solution of 2-hydroxymethyl-5-(2-methoxyphenyl)-N-(carbobenzyloxy)-tetrahydroopyrrole (2.49 g, 7.30 mmol) in DMF (20 mL) at 0–40° C. was added methyl iodide (4.55 mL, 73 mmol) and NaH (60% oil dispersion, 1.75 g, 43.8 mmol) and the resulting suspension was stirred at room temperature for 1 hour. The reaction mixture was quenched with $H_2O$ at 0° C., ether was added, and the aqueous layer was extracted with ether (x4), and the combined organic layers were washed with brine, dried over anhydrous $Na_2SO_4$, and concentrated in vacuo. The crude product was purified by silica gel flash chromatography (5% EtOAc-95% hexanes) to provide the title compound as a colorless oil. $^1H$ NMR (CDCl$_3$, 400 MHz) δ: 3.77 (3H, s, OMe), 3.38 (3H, s, OMe).

PREPARATION 22

2-Methoxymethyl-5-(2-methoxvphenyl)-tetrahydropyrrole

To a solution of 2-methoxymethyl-5-(2-methoxyphenyl)-N-(carbobenzyloxy)-tetrahydropyrrole (1.3 g, 3.66 mmol) in methanol (40 mL) was added 10% Pd-C (1.3 g) and the resulting suspension was hydrogenated (50 psi) for 3 hours. Pd-C was then filtered off and the crude reaction mixture was concentrated in vacuo to give a yellowish residue, which was purified by silica gel flash chromatography (5% MeOH-0.5% NH$_3$♦H$_2$O-94.5% CH$_2$Cl$_2$) to afford the title compound as a colorless oil (439.2 mg, 54%). MS m/z: 222 (M+H).

PREPARATION 23

2-Methoxymethyl-5-(2-methoxyphenyl)-N-(2-phthalmidoethyl)-tetrahydropyrrole

To a solution of 2-methoxymethyl-5-(2-methoxyphenyl)-tetrahydropyrrole (226 mg, 1.02 mmol) in CH$_2$Cl$_2$ was added NaOAc (88 mg, 1.07 mmol), N-phthalimidoacetaldehyde (203 mg, 1.07 mmol) and NaB(OAc)$_3$H (326 mg, 1.54 mmol) and the resulting suspension was stirred at ambient temperature for 17 hours. H$_2$O was added followed by 1N NaOH until pH was 10, the aqueous layer was extracted with CHCl$_3$ (x4), and the combined organic layers were washed with brine, dried over MgSO$_4$ and evaporated in vacuo. The crude product was purified by silica gel flash chromatography (5% MeOH-0.5% NH$_3$·H$_2$O-94.5% CH$_2$Cl$_2$) to afford the title compound as a yellow oil (348 mg, 86%). MS mfz: 395 (M+H)

PREPARATION 24

2-Methoxymethyl-5-(2-methoxyphenyl-1-(2-aminoethyl)-tetrahvdropyrrole

To a solution of 2-methoxymethyl-5-(2-methoxyphenyl)-(2-phthalimidoethyl)-tetrahydropyrrole (333 mg, 0.85 mmol) in ethanol (5 mL) was added anhydrous hydrazine (80 µl, 2.5 mmol). The resulting suspension was stirred at room temperature for 3 days The reaction mixture was filtered through Celite™, and the solid was washed with methanol (40 mL).

The filtrate was concentrated in vacuo, the residue was triturated with CH$_2$Cl$_2$ (40 mL) and filtered to remove any remaining byproduct. The filtrated was again concentrated to afford the title compound as a light yellow oil (211 mg). MS m/z: 265(M+H).

PREPARATION 25

2-Methoxyphenyl4 hydroxypiperidine

To a solution of N-benzyl-2,3-dihydro-2-(2-methoxyphenyl)4-pyridone (5.5 g, 18.77 mmol) (which was prepared by the procedures of Yamamoto et al., Tetrahedron, 1993, 49, 1749) in methanol (80 mL) was added Pd(OH)$_2$ (1.7 9) and the resulting suspension was hydrogenated (50 psi) for 20 hours. Pd-C was then filtered off and the crude reaction mixture was concentrated in vacuo to give a residue, which was purified by silica gel flash chromatography (5% MeOH-0.5% NH$_3$♦H$_2$O-94.5% CH$_2$Cl$_2$) to afford the title compound as a solid (1.5g). $^{13}$C NMR (CDCl$_3$, 100 MHz) ) δ:156.5, 131.4, 128.1, 126.9, 120.8, 110.3, 69.6, 55.3, 53,8, 45.1, 41.7, and 35.6.

PREPARTION 26

N-(tert-Butoxycarbonyl)-2-(2-Methoxyphenyl)-4-hydroxypiperidine

To a solution of 2-(2-methoxyphenyl)4-hydroxypiperidine (1.15 g, 5.66 mmol) in CH$_2$Cl$_2$ (10 mL) was added di-tert-butyl dicarbonate (1.3 g, 5.94 mmol) and the resulting solution was stirred at room temperature for 30 minutes. The solution was evaporated in vacuo and the residue was dissolved in ether and H$_2$O. The aqueous layer was extracted with ether (x4), the combined ether layers were washed with brine, dried over Na$_2$SO$_4$, and evaporated in vacuo to give the title compound as a colorless oil (0.9 g). $^1$H NMR (CDCl$_3$, 400 MHz) δ:3.81 (3H, s, OMe), 1.24 (9H, Bu-t).

PREPARATION 27

N-(tert-Butoxycarbonyl)-2-(2-Methoxvphenyl) Amethoxvpiperidine

To a solution of N-(tert-butoxycarbonyl)-2-(2-methoxyphenyl)-4-hydroxypiperidine (910 mg, 2.94 mmol) in DMF (10 mL) at 0° C. was added methyl iodide (0.92 mL, 14.8 mmol) and NaH (236 mg, 5.9 mmol) and the resulting suspension was stirred at room temperature for 2 hours. The reaction mixutre was quenched with H$_2$O at 0° C., EtOAc was added, and the aqueous layer was extracted with EtOAc (x4). The combined organic layers were washed with brine, dried over anhydrous Na$_2$SO$_4$, and concentrated in vacuo to provide the title compound as a colorless oil (898 mg). $^1$H NMR (CDCl$_3$, 400 MHz) 8:3.82 (3H, s, OMe), 3.10 (3H, s, OMe), and 1.22 (9H, s, Bu-t).

PREPARATION 28

2-(2-Methoxyphenyl)4-methoxypiperidine

To a solution of N-(tert-butoxycarbonyl)-2-(2-methoxyphenyl)-4-methoxypiperidine (864 mg, 2.67 mmol) in CH$_2$Cl$_2$ at 0° C. was added TFA (9.6 mL) and the resulting solution was stirred at 0–40° C. for 2 hours. TFA was removed in vacuo, and the residue was stirred with 40 mL of 1:1 mixture of CH$_2$Cl$_2$ and 1N NaOH for 20 minutes. The layers were separated and the aqueous layer was extracted with CH$_2$Cl$_2$ (3×15 ml). The combined organic layers were washed with brine, dried over MgSO$_4$, and concentrated in vacuo to afford the title compound as a light brown oil (565 mg). $^1$H NMR (CDCl$_3$, 400 MHz) δ: 3.82 (3H, s, OMe), 3.37 (3H, s, OMe).

PREPARATION 29

N-(2-Aminoethyl)-2-(2-methoxyphenyl)-4-methoxypiperidine 2-(2-Methoxyphenyl)4-methoxypiperidine was converted to the title compound in two steps by the same procedures as the transformation of 2-methoxymethyl-5-(2-methoxyphenyl)-tetrahydropyrrole to 2-methoxymethyl-5-(2-methoxyphenyl)-1-(2-aminoethyl)-tetrahydropyrrole as described above in Preparations 23 and 24. $^1$H NMR (CDCl$_3$, 400 MHz) δ:3.80 (3H, s, OMe), 3.31 (3H, s, OMe).

PREPARATION 30

N-(2-Aminoethyl)-7,8-dimethoxy-1,2,3,4-tetrahydroisoguinoline.

To a solution of 7,8-dimethoxy-1,2,3,4-tetrahydroisoquinoline (421 mg, 2.2 mmol), 2-phthalimidoacetaldehyde (410 mg, 2.2 mmol) and NaOAc (180 mg, 2.2 mmol) in 27 mL of CH$_2$Cl$_2$ was added 690 mg (3.25 mmol) of NaBH(OAc)$_3$ in small portions. After stirring 1 hour at room temperature, the reaction mixture was diluted with CH$_2$Cl$_2$ and washed with a saturated Na$_2$CO$_3$ solution and brine. The residue obtained after evaporation of $CH_2Cl_2$ was dissolved in 25 mL of EtOH and treated with 1.2 mL of hydrazine hydrate overnight. The reaction mixture was then filtered and evaporated to give 510 mg (100%) of the title compound; MS m/e 327 (M+1).

PREPARATION 31

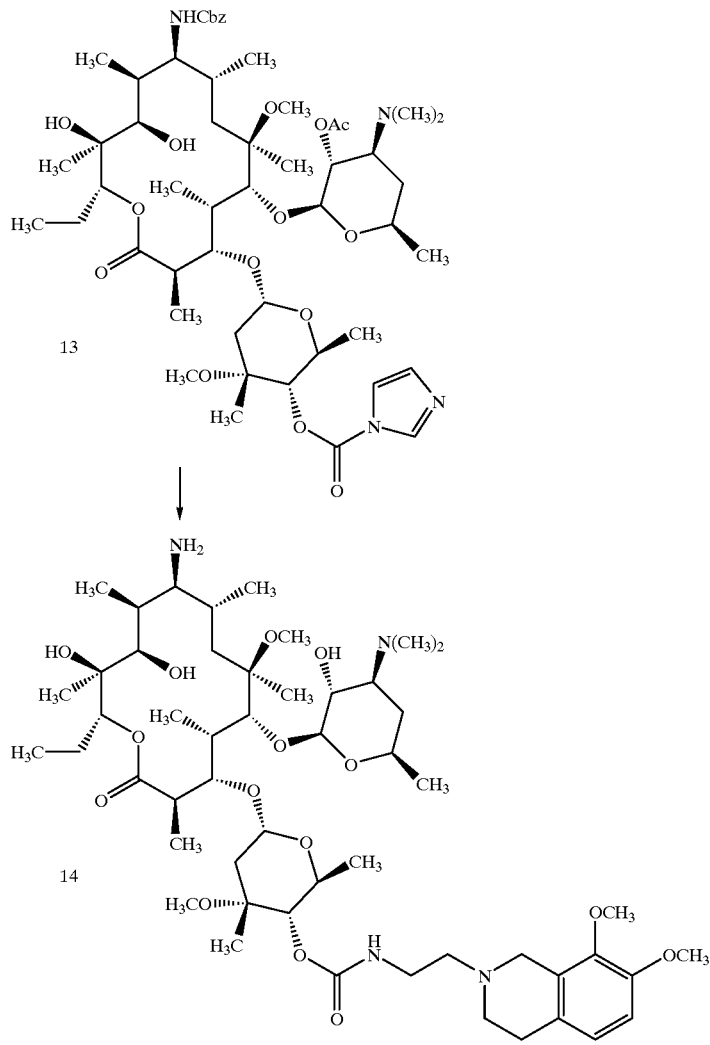

A solution of $N_9$-Cbz-2'-acetyl4"-imidazolcarbonylerythromycylamine (the compound of formula 13) (300 mg., 0.31 mmol) and N-(2-aminoethyl)-7,8-dimethoxy-1,2,3,4-tetrahydroisoquinoline (109 mg, 0.46 mmol) in 5 mL of DMSO containing 47 mg of $K_2CO_3$ was warmed to 60° C. for 6 hours then stirred at room temperature overnight. The reaction mixture was diluted with EtOAc and washed with brine. Drying over $MgSO_4$ and removal of the solvent gave a slightly yellow solid. This was dissolved in 4 mL of $CH_2Cl_2$ and treated with lutidine (0.43 mL, 3.7 mmol) and TMSOTf (0.48 mL, 2.5 mmol) at 0° C. for 2 hours. The reaction mixture was washed with a dilute NaCl solution and dried over $MgSO_4$. The residue obtained was then dissolved in 4mL of THF and treated with 3.1 mL of 1M solution of tetrabutylammonium fluoride in THF, initially at 0° C. and at room temperature for 24 hours. THF was removed and the residue was dissolved in $CH_2Cl_2$ and water.

The aqueous layer was acidified to pH 2 and extracted. The aqueous layer was then basified to pH 9 and extracted with $CH_2Cl_2$. This $CH_2Cl_2$ layer was washed with brine and dried over $MgSO_4$. The residue obtained was dissolved in 4 mL of MeOH and refluxed overnight. A $SiO_2$ chromatography (4% MeOH-$CH_2Cl_2$ –0.4% $NH_4OH$) of the residue gave 96 mg (31%) of the compound of formula 14 MS m/e 1039 (M+1).

PREPARATION 32

N-(N'-Boc-Glycyl)4-methoxy-1,2,3,4-tetrahydroisoquinoline.

To a solution of 4-methoxy-1,2,3,4-tetrahydroisoquinoline (5.88 g, 36 mmol) in 100 mL of $CH_2Cl_2$ were added Boc-glycine (12.6 g, 72 mmol), 4dimethylaminopyridine (8.80 g, 72 mmol), and dicyclohexyl carbodiimide (14.9 g, 72 mmol). After stirring overnight, the resulting precipitate was filtered and the filtrate was evaporated. A $SiO_2$ chromatography (EtOAc:hexane =1:1) of the residue gave 4.9 9 (43%) of the title compound.

PREPARATION 33

N-(2-Aminoethyl)4-methoxy-1,2,3,4-tetrahydroisoguinoline.

A solution of N-(N'-Boc-glycyl)4-methoxy-1,2,3,4-tetrahydroisoguinoline (4.97 g, 16 mmol) in 30 mL of 3 N HCl and 30 mL of EtOAc was heated to reflux for 0.5 hour. The resulting solution was basified to pH 9 and extracted with EtOAc. The aqueous layer was then extracted with 10% iPrOH- $CH_2Cl_2$. Drying over MgSO4 of the iPrOH-$CH_2Cl_2$ solution and removal of the solvent gave 2.83 g (89%) of N-glycyl4-methoxy-1,2,3,4tetrahydroisoquinoline.

A solution of N-glycyl4-methoxy-1,2,3,4-tetrahydroisoquinoline in 25 mL of THF was cooled in an ice bath and 10 M solution of borane-methyl sulfide complex in THF (3.85 mL) was added dropwise. The resulting mixture was warmed to 55° C. and then to reflux for 4 hours. Excess borane was destroyed by addition of 6N HCl. The resulting mixture was heated to 100° C. for 1 hour. The resulting solution was first extracted with EtOAc and then with 10% iPrOH—$CH_2Cl_2$. The iPrOH—$CH_2Cl_2$ extract gave 880 mg (28%) of the title compound.

PREPARATION 34

A solution of 2'-acetyl-4"-imidazolecarbonylclarithromycin-11,12-cyclic carbamate (the compound of formula 15 (200 mg, 0.22 mmol) and N-(2-aminoethyl)4-methoxy-1,2,3,4-tetrahydroisoquinoline (91 mg, 0.44 mmol) in 2 mL of THF was refluxed for two days. A $SiO_2$ chromatography (3% MeOH-$CH_2Cl_2$—0.5% $NH_4OH$) of the residue gave 183 mg of a colorless solid. This material was refluxed overnight in 4 mL of MeOH to give 149 mg (69%) of the compound of formula 16; MS m/e 1005 (M+1).

PREPARATION 35

Following the procedure of Preparation 34 and starting with N-(2-aminoethyl)-7,8-dimethoxy-1,2,3,4-tetrahydroisoquinoline, the compound of formula 16 was obtained with 7,8-dimethoxy-1,2,3,4-isoquinoline in place of 4-methoxy-1,2,3,4-isoquinoline, in 81% yield; MS m/e 1035 (M+1).

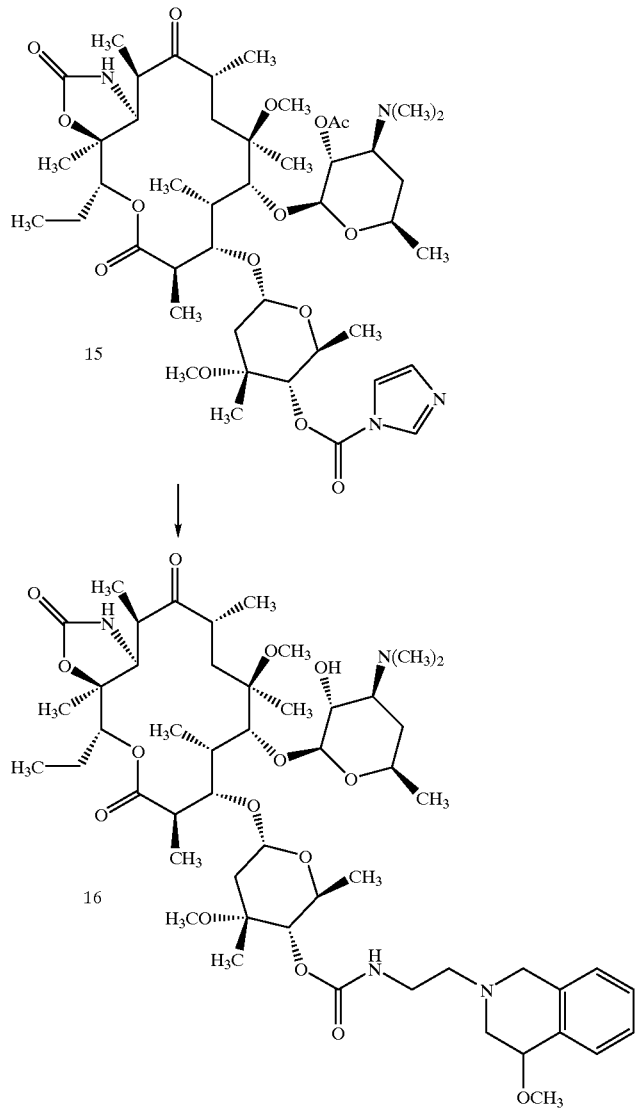

PREPARATION 36

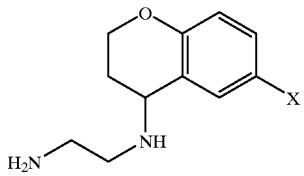

17

Following the procedure of Preparation 30 and starting with 6-(un)substituted 4-amino-chroman, ethylenediamine of formula 17 were prepared wherein X is a substituent such as a fluoro group or unsubstituted at that position.

PREPARATION 37

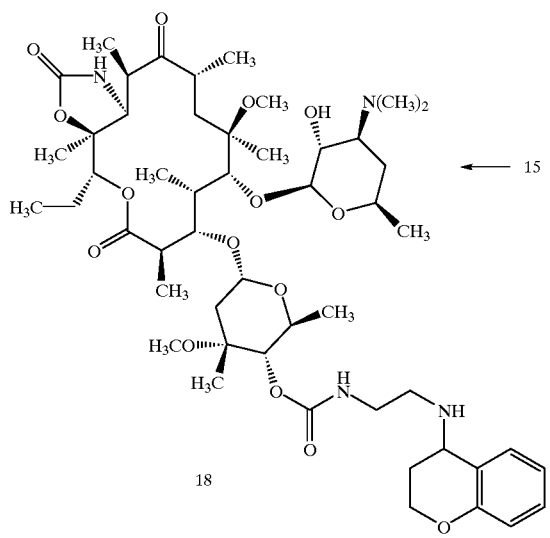

18

Following the procedure of Preparation 34 and starting with N-(2-aminoethyl)+amino-chroman and the compound of formula 15, the above compound of formula 18 was obtained in 87% yield; MS m/e 991 (M+1).

PREPARATION 38

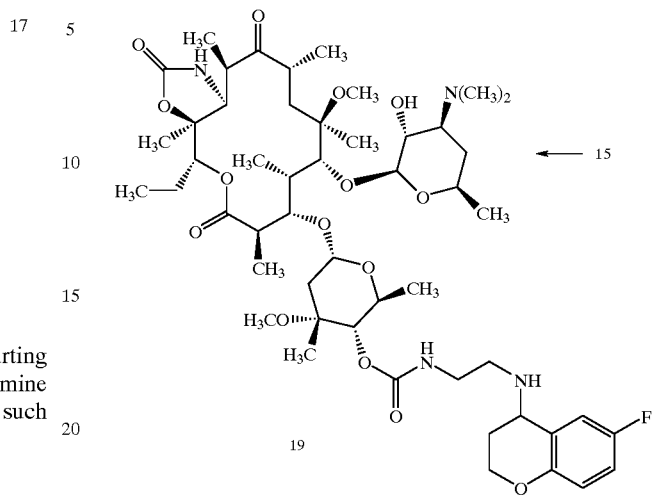

19

Following the procedure of Preparation 34 and starting with N-(2-aminoethyl)-4amino-6-fluorochroman and the compound of formula 15 the above compound of formula 19 was obtained in 34% yield; MS m/e 1009 (M+1).

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. All such isomers, including diastereomer mixtures, are considered as part of the invention.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Altematively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The antibacterial and antiprotozoal activity of the compounds of the present invention against bacterial and protozoal pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology andlor by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microliter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as stock solutions.

| Strain Designation | Macrolide Resistance Mechanism(s) |
|---|---|
| Staphylococcus aureus 1116 | susceptible parent |
| Staphylococcus aureus 1117 | ermB |
| Staphylococcus aureus 0052 | susceptible parent |
| Staphylococcus aureus 1120 | ermC |
| Staphylococcus aureus 1032 | msrA, mph, esterase |
| Staphylococcus hemolyticus 1006 | msrA, mph |
| Streptococcus pyogenes 0203 | susceptible parent |
| Streptococcus pyogenes 1079 | ermB |
| Streptococcus pyogenes 1062 | susceptible parent |
| Streptococcus pyogenes 1061 | ermB |
| Streptococcus pyogenes 1064 | ermB |
| Streptococcus agalactiae 1024 | susceptible parent |
| Streptococcus agalactiae 1023 | ermB |
| Streptococcus pneumoniae 1016 | susceptible |
| Streptococcus pneumoniae 1046 | ermB |
| Streptococcus pneumoniae 1095 | ermB |
| Streptococcus pneumoniae 1175 | mefE |
| Streptococcus pneumoniae 0085 | susceptible |
| Haemophllus influenzae 0131 | susceptible |
| Moraxella catarrhalis 0040 | susceptible |
| Moraxella catarrhalis 1055 | erythromycin intermediate resistance |
| Eschedchia coli 0266 | susceptible |

Assay II is utilized to test for activity against Pasteurella multocida and Assay IIIl is utilized to test for activity against *Pasteurella haemolytica*.

Assay II

This assay is based on the liquid dilution method in microliter format A single colony of *P. multocida* (strain 59A067) is inoculated into 5 ml of brain heart infusion (BHI) broth. The test compounds are prepared by solubilizing 1 mg of the compound in 125 $\mu$l of dimethylsulfoxide (DMSO). Dilutions of the test compound are prepared using uninoculated BHI broth. The concentrations of the test compound used range from 200 $\mu$g/ml to 0.098 $\mu$g/ml by two-fold serial dilutions. The *P. multocida* inoculated BHI is diluted with uninoculated BHI broth to make a $10^4$ cell suspension per 200 $\mu$l. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 $\mu$l of the fully grown *P. haemolyfica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 $\mu$l of the *P. haemolytica* culture is inoculated onto BHI agar plates containing the various concentrations of the test compound using a Steers Replicator and incubated for 18 hours at 37° C. Initial concentrations of the test compound range from 100–200 $\mu$g/ml. The MIC is equal to the concentration of the test compound exhibiting 100% inhibition of growth of *P. haemolytica* as determined by comparison with an uninoculated control.

The in vivo activity of the compounds of the present invention can be determined by conventional animal protection studies well known to those skilled in the art, usually carried out in rodents.

According to one in vivo model, mice are allotted to cages upon their arrival, and allowed to acclimate before being used. Animals are inoculated with a bacterial suspension (*P. multocida* strain 59A006) intraperitoneally. Each experiment has at least 3 non-medicated control groups including one infected with 0.1X challenge dose and two infected with 1X challenge dose; a 10X challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given.

The compounds of the present invention, and the pharmaceutically acceptable salts thereof (hereinafter "the active compounds"), may be adminstered through oral, parenteral, topical, or rectal routes in the treatment of bacterial and protozoal infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

In the treatment of cancer, in particular non-small cell lung cancer, the active compounds may be administered as described in European patent application publication number 758,549, published Feb. 2, 1997.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral adinistraton, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be adminstered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The present invention is further described and exemplified in the preparations and examples described below.

In the tables provided below, the compounds were prepared according to the procedures described above. In the tables, "Mac" refers to the specific macrolide templates referred to above the tables, "Scheme" refers to the general method by which each compound exemplified was prepared (e.g., "Scheme" 2 means the method of preparation described for Scheme 2), and "Mass Spec" refers to the mass spectra of each compound exemplified.

In Examples 3, 22, 39, 41, 44–49, 105, 119, 128 and 129 of Table 2, substituents $Y^3$ and $Y^4$ are taken together with the nitrogen to which each substituent is attached to form the cyclic moiety illustrated for each example. In Examples 149, 154, 155, 160, 161, 237, 238 and 239, $Y^1$ and $Y^2$ are taken together with the nitrogen to which each is attached to form a double bond as illustrated for the moieties shown for each example. In Examples 108 and 156 of Table 2, the designation "M-12 (9R)" indicates the R configuration at the G9 carbon of the M-12 macrolide template. Otherwise, the configuration at the C-9 carbon for the M-12 template is as shown below. In Examples 116 and 117 of Table 2, the designation M-12 "(6-MeO)" indicates that the hydroxy at the C-6 carbon of the M-12 macrolide template is replaced with a methoxy group.

TABLE 1

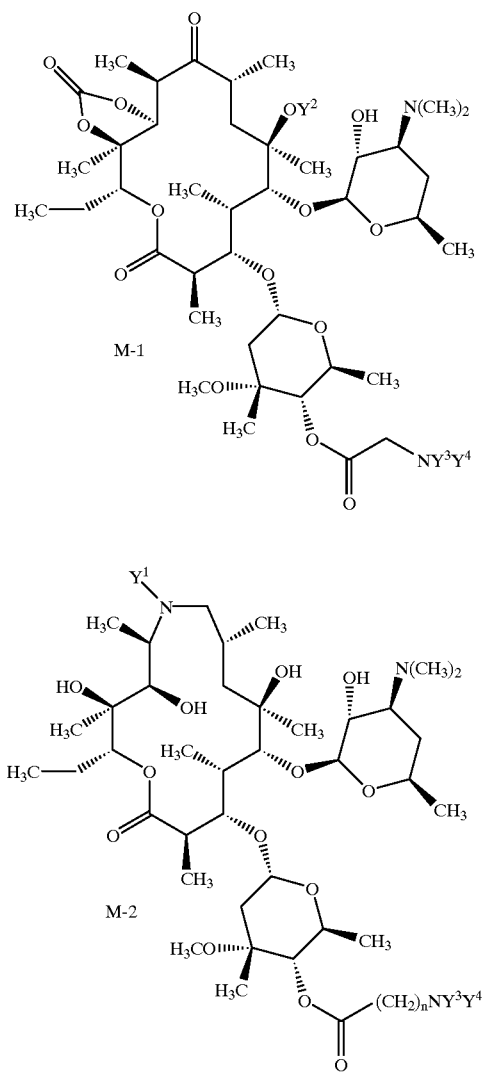

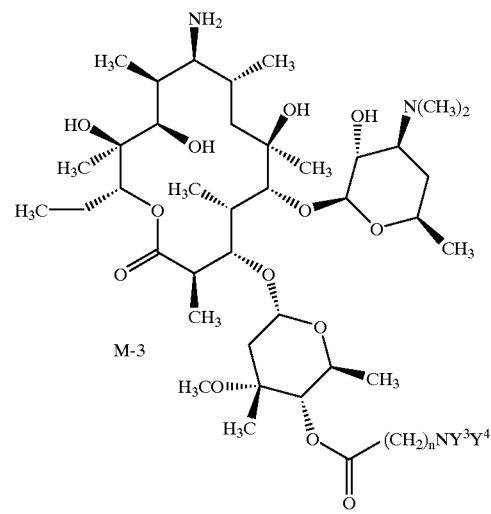

M-3

| Ex | Mac | Y¹ | Y² | n | Y³ | Y⁴ | Scheme | Mass Spec (M + 1) |
|---|---|---|---|---|---|---|---|---|
| 1 | M-1 | — | H | — | 2-naphthoyl | H | 2 | 972 |
| 2 | M-2 | $CH_3$ | — | 1 | 2-naphthoyl | H | 2 | 961 |
| 3 | M-2 | $CH_3$ | — | 1 | (E)-3-(4-methoxyphenyl)acryloyl | H | 2 | 966 |
| 4 | M-2 | $CH_3$ | — | 1 | benzo[b]thiophene-2-carbonyl | H | 2 | 966 |
| 5 | M-2 | $CH_3$ | — | 1 | 2-chloro-6,7-dimethoxyquinazolin-4-yl | H | 2 | 1030 |
| 6 | M-1 | — | $CH_3$ | — | benzyl | H | 2 | 922 |
| 7 | M-1 | — | $CH_3$ | — | 8-quinolinesulfonyl | H | 2 | 1023 |
| 8 | M-2 | $CH_3$ | — | 3 | 2,4-dimethoxybenzyl | 2,4-dimethoxybenzyl | 2 | 1135 |
| 9 | M-2 | $CH_3$ | — | 3 | H | 3-(4-chlorophenoxy)benzyl | 2 | 1052 |
| 10 | M-3 | — | — | 2 | H | 2,4-dimethoxybenzyl | 2 | 957 |
| 11 | M-3 | — | — | 2 | 2,4-dimethoxybenzyl | 2,4-dimethoxybenzyl | 2 | 1107 |
| 12 | M-3 | — | — | 2 | 3-methoxybutyl | 2-methoxybenzyl | 2 | 1013 |
| 13 | M-3 | — | — | 2 | 3-methoxybutyl | 2,4-dimethoxybenzyl | 2 | 1043 |
| 14 | M-2 | $CH_3$ | — | 3 | methyl | 2-methoxybenzyl | 2 | 969 |
| 15 | M-2 | $CH_3$ | — | 3 | propyl | 2-methoxybenzyl | 2 | 997 |
| 16 | M-2 | $CH_3$ | — | 3 | ethyl | 2-methoxybenzyl | 2 | 983 |
| 17 | M-2 | $CH_3$ | — | 3 | ethyl | 2,4-dimethoxybenzyl | 2 | 1014 |
| 18 | M-2 | $CH_3$ | — | 3 | 2-ethoxyethyl | 2-methoxybenzyl | 2 | 1027 |

| 19 | M-2 | CH₃ | — | 3 | H | 1-(2-methoxyphenyl)ethyl | 2 | 969 |
| 20 | M-2 | CH₃ | — | 3 | H | 2,4-dimethoxybenzyl | 2 | 955 |
| 21 | M-2 | CH₃ | — | 3 | methyl | 1-(2-methoxyphenyl)ethyl | 2 | 983 |
| 22 | M-2 | CH₃ | — | 3 | H | 2,4-dimethoxybenzyl | 2 | 985 |
| 23 | M-2 | CH₃ | — | 3 | ethyl | 1-(2-methoxyphenyl)ethyl | 2 | 997 |
| 24 | M-2 | CH₃ | — | 3 | isopropyl | 2-methoxybenzyl | 2 | 997 |
| 25 | M-3 | — | — | 2 | H | 2-methoxybenzyl | 2 | 927 |
| 26 | M-2 | CH₃ | — | 3 | methyl | 1-(2-methoxyphenyl)ethyl | 2 | 1013 |
| 27 | M-3 | — | — | 3 | ethyl | 1-(2-methoxyphenyl)ethyl | 2 | 983 |
| 28 | M-2 | CH₃ | — | 3 | H | 1-(2,4-dimethoxyphenyl)ethyl | 2 | 999 |
| 29 | M-3 | — | — | 3 | methyl | 1-(2,4-dimethoxyphenyl)ethyl | 2 | 969 |
TABLE 2
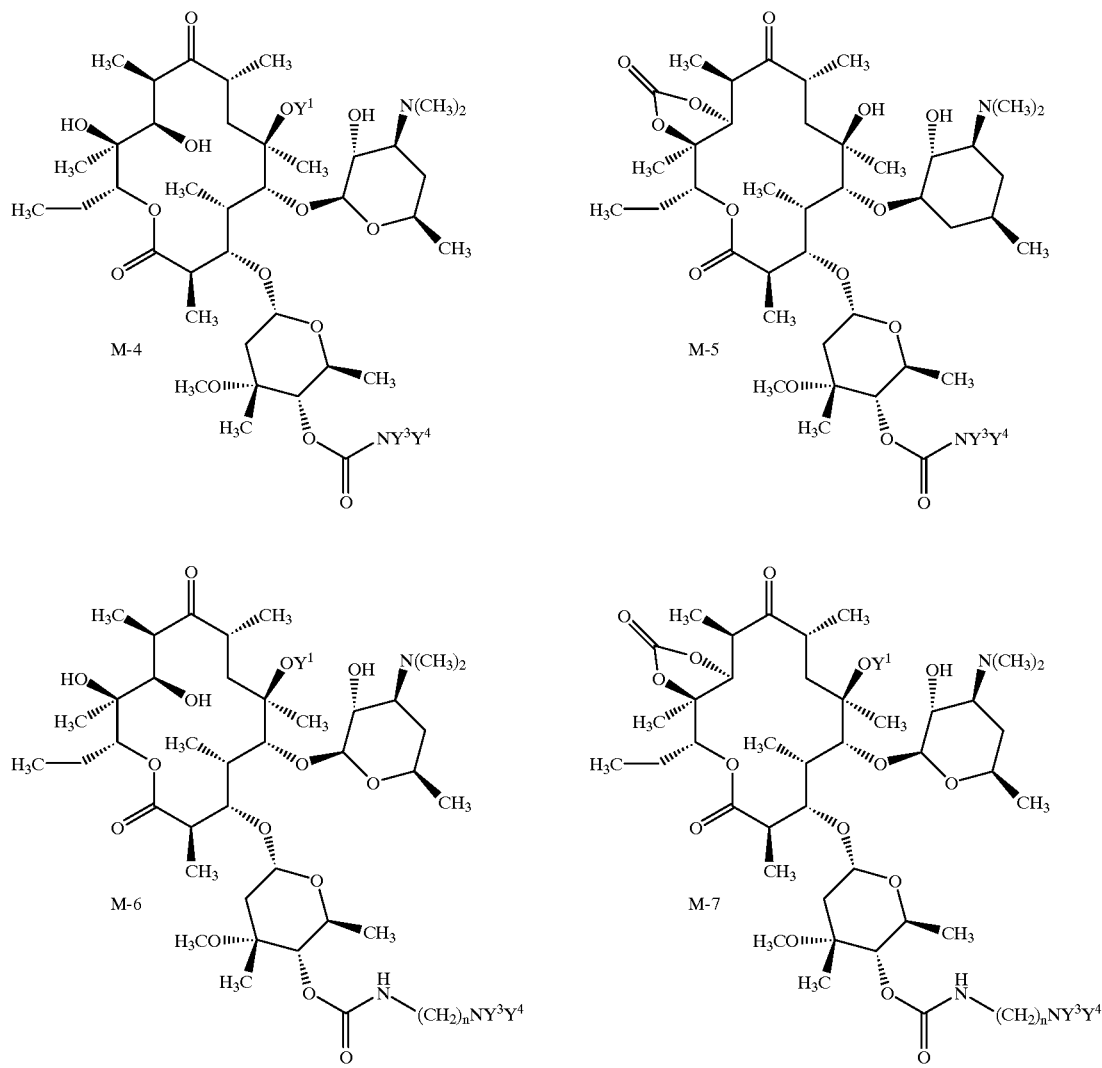

TABLE 2-continued
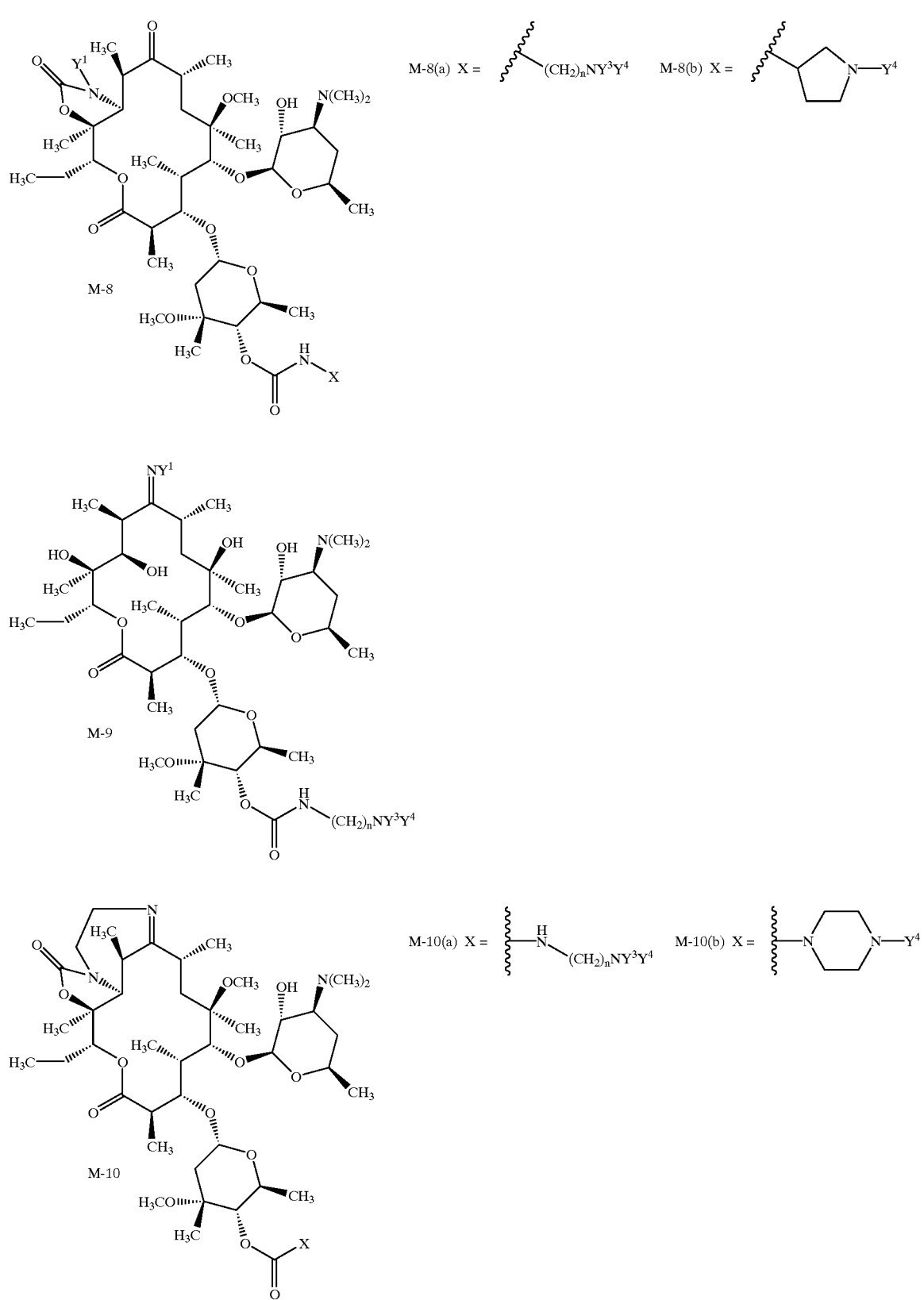

TABLE 2-continued
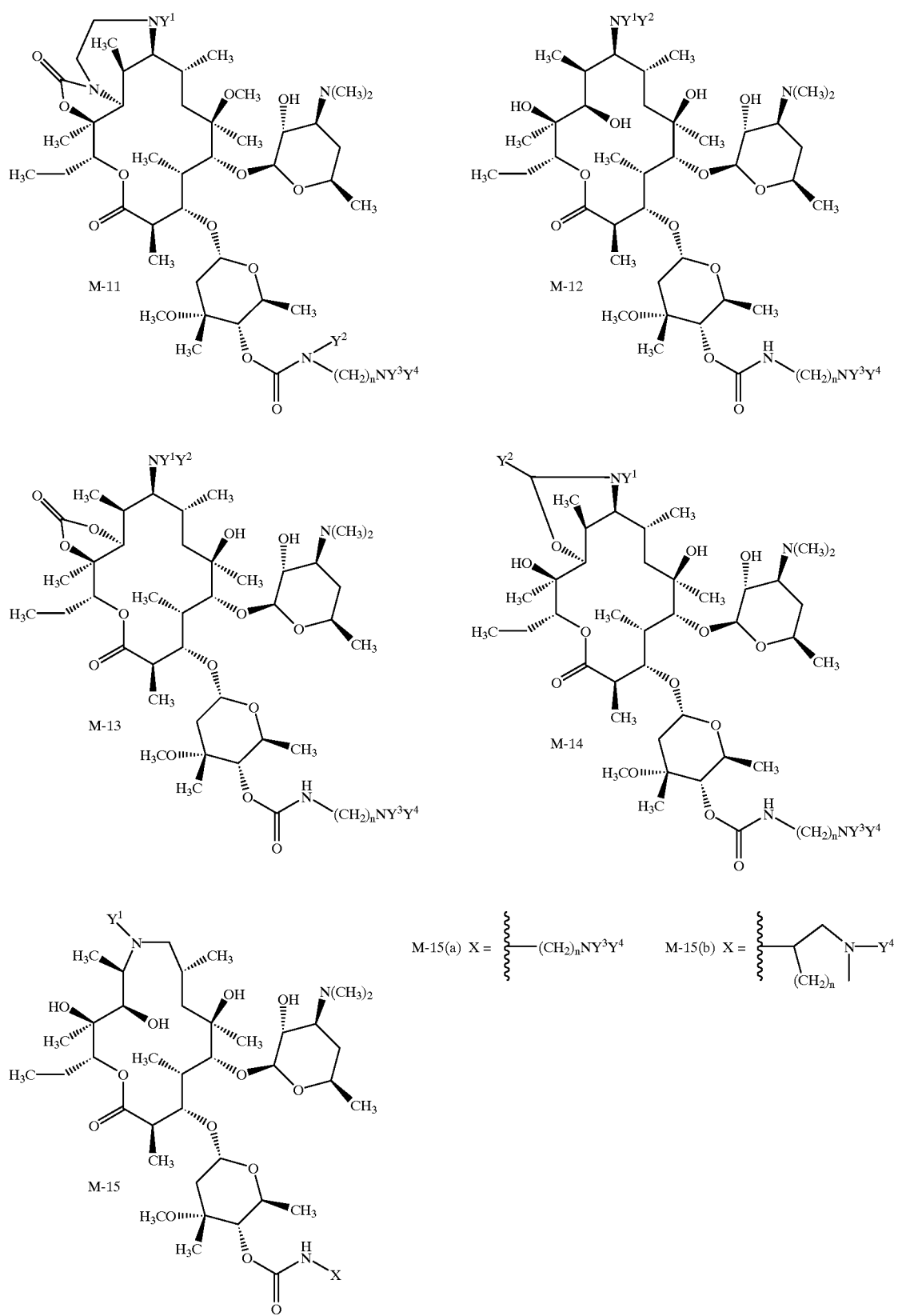

TABLE 2-continued

Structures M-16, M-17, M-18 (macrolide derivatives with carbamate side chains).

| Ex | Mac | Y¹ | Y² | n | Y³ | Y⁴ | Scheme | Mass Spec |
|---|---|---|---|---|---|---|---|---|
| 1 | M-4 | H | — | — | H | 3-fluorophenyl | 3,2 | 872 (M + 1) |
| 2 | M-4 | CH₃ | — | — | H | 2-(2-methoxybenzyloxy)ethyl | 3,2 | 955 (M + 1) |
| 3 | M-4 | CH₃ | — | | | (2-methoxybenzyl)piperazinyl structure | 3,2 | 980 (M + 1) |
| 4 | M-5 | — | — | — | H | 3-nitrophenyl | 3,2 | 925 (M + 1) |
| 5 | M-5 | — | — | — | H | 3-nitrophenyl | 3,2 | 895 (M + 1) |
| 6 | M-6 | CH₃ | — | 2 | 2,4-dimethoxybenzyl | 2,4-dimethoxybenzyl | 3,2 | 1134 (M + 1) |
| 7 | M-6 | CH₃ | — | 2 | H | 2-fluorobenzyl | 3,2 | 943 (M + 1) |
| 8 | M-6 | CH₃ | — | 2 | H | 2,4-dimethylthiazol-5-yl carbonyl | 3,2 | 974 (M + 1) |
| 9 | M-6 | CH₃ | — | 2 | H | 2,4-dimethyl-5- | 3,2 | 960 (M + 1) |

TABLE 2-continued

| | | | | | | | | | |
|---|---|---|---|---|---|---|---|---|---|
| | | | | | | thiazolylmethyl | | | |
| 10 | M-6 | CH₃ | — | 2 | H | 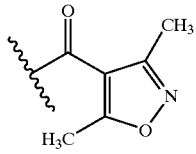 | | 3,2 | 958 (M + 1) |
| 11 | M-8 (a) | H | — | 2 | 2,4-dimethoxybenzyl | 2,4-dimethoxybenzyl | | 3,2 | 1160 (M + 1) |
| 12 | M-8 (a) | H | — | 2 | 2-methoxybenzyl | 2-methoxybenzyl | | 3,2 | 1100 (M + 1) |
| 13 | M-8 (a) | H | — | 2 | 2-methoxyethyl | 2-methoxyethyl | | 3,2 | 976 (M + 1) |
| 14 | M-8 (a) | H | — | 2 | 2-methoxyethyl | 2-methoxybenzyl | | 3,2 | 1039 (M + 1) |
| 15 | M-8 (a) | H | — | 2 | 2-methoxybenzyl | cyclohexylmethyl | | 3,2 | 1076 (M + 1) |
| 16 | M-8 (a) | H | — | 2 | 3-methoxybutyl | 3-methoxybutyl | | 3,2 | 1032 (M + 1) |
| 17 | M-8 (a) | H | — | 2 | H | 2-methoxyethyl | | 3,2 | 918 (M + 1) |
| 18 | M-8 (a) | H | — | 2 | H | 2-methoxybenzyl | | 3,2 | 980 (M + 1) |
| 19 | M-8 (a) | H | — | 2 | H | 1-methyl-2-pyrrolylmethyl | | 3,2 | 953 (M + 1) |
| 20 | M-8 (a) | H | — | 2 | H | 2-furylmethyl | | 3,2 | 940 (M + 1) |
| 21 | M-8 (a) | H | — | 2 | H | 3-furylmethyl | | 3,2 | 940 (M + 1) |
| 22 | M-8 (a) | H | — | 2 | | 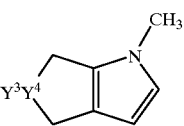 | | 3,2 | 965 (M + 1) |
| 23 | M-8 (a) | H | — | 2 | H | 2-(2-methoxyethoxy)-benzyl | | 3,2 | 1024 (M + 1) |
| 24 | M-8 (a) | H | — | 2 | H | 2-methoxy-3-pyridylmethyl | | 3,2 | 981 (M + 1) |
| 25 | M-8 (a) | H | — | 2 | H | 3-(2-furyl)-2-propenyl | | 3,2 | 966 (M + 1) |
| 26 | M-8 (a) | H | — | 2 | H | 2-pyrrolylmethyl | | 3,2 | 939 (M + 1) |
| 27 | M-8 (a) | H | — | 2 | H | 3,5-dimethyl-4-isoxazolylmethyl | | 3,2 | 969 (M + 1) |
| 28 | M-8 (a) | H | — | 2 | H | 2-methoxybenzoyl | | 3,2 | 994 (M + 1) |
| 29 | M-8 (a) | H | — | 2 | methyl | 3,5-dimethyl-4-isoxazolylmethyl | | 3,2 | 983 (M + 1) |
| 30 | M-8 (a) | H | — | 2 | H | 3-furoyl | | 3,2 | 954 (M + 1) |
| 31 | M-8 (a) | H | — | 2 | H | 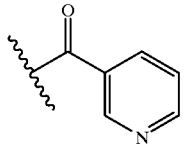 | | 3,2 | 965 (M + 1) |
| 32 | M-8 (a) | H | — | 2 | H | 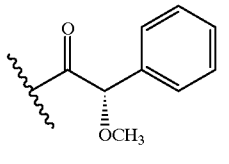 | | 3,2 | 983 (M + 1) |
| 33 | M-8 (a) | H | — | 2 | H | 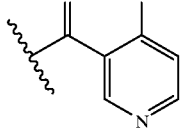 | | 3,2 | 981 (M + 1) |
| 34 | M-8 (a) | H | — | 2 | 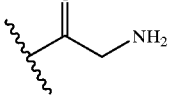 | 2-methoxybenzyl | | 3,2 | 1037 (M + 1) |
| 35 | M-8 (a) | H | — | 2 | H | 1-(2-hydroxyphenyl)ethyl | | 3,2 | 980 (M + 1) |

TABLE 2-continued
| | | | | | | | | |
|---|---|---|---|---|---|---|---|---|
| 36 | M-8 (a) | H | — | 2 | 2-hydroxyethyl | 2-methoxybenzyl | 3,2 | 1024 (M + 1) |
| 37 | M-8 (a) | H | — | 2 | 2,2,2-trifluoroethyl | 2-hydroxybenzyl | 3,2 | 1048 (M + 1) |
| 38 | M-8 (a) | H | — | 2 | 2,2,2-trifluoroethyl | 2,5-dimethyl-4-oxazolylmethyl | 3,2 | 1051 (M + 1) |
| 39 | M-8 (a) | H | — | 2 | | 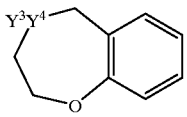 | 3,2 | 992 (M + 1) |
| 40 | M-8 (a) | H | — | 2 | H | 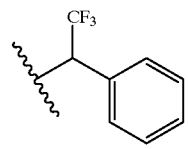 | 3,2 | 1018 (M + 1) |
| 41 | M-8 (a) | H | — | 2 | | 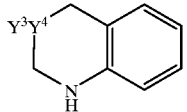 | 3,2 | 977 (M + 1) |
| 42 | M-8 (a) | H | — | 2 | $CH_3$ | 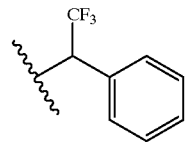 | 3,2 | 1032 (M + 1) |
| 43 | M-8 (a) | H | — | 2 | $CH_3$ | 2-methoxybenzyl | 3,2 | 994 (M + 1) |
| 44 | M-8 (a) | H | — | 2 | | 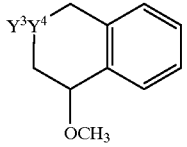 | 3,2 | 1005 (M + 1) |
| 45 | M-8 (a) | H | — | 2 | | 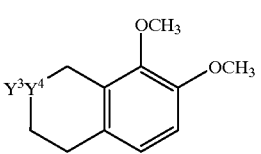 | 3,2 | 1035 (M + 1) |
| 46 | M-8 (a) | H | — | 2 | | 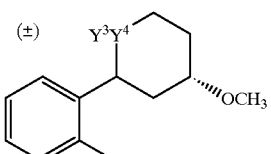 | 3,2 | 1064 (M + 1) |
| 47 | M-8 (a) | H | — | 2 | | 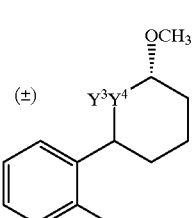 | 3,2 | 1064 (M + 1) |

TABLE 2-continued

| | | | | | | | | |
|---|---|---|---|---|---|---|---|---|
| 48 | M-8 (a) | H | — | 2 | | 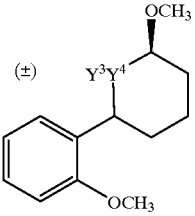 | 3,2 | 1064 (M + 1) |
| 49 | M-8 (a) | H | — | 2 | | 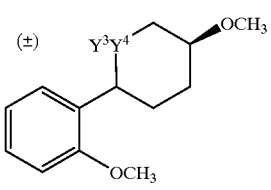 | 3,2 | 1064 (M + 1) |
| 50 | M-8 (a) | H | — | 2 | H | 1-methyl-1-(2-methoxyphenyl)ethyl | 3,2 | 1008 (M + 1) |
| 51 | M-8 (a) | H | — | 2 | H | 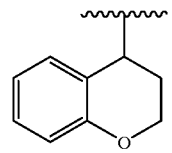 | 3,2 | 991 (M + 1) |
| 52 | M-8 (a) | H | — | 2 | H | 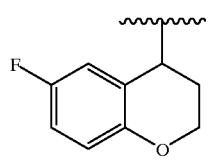 | 3,2 | 1009 (M + 1) |
| 53 | M-8 (a) | H | — | 2 | CH₃ | 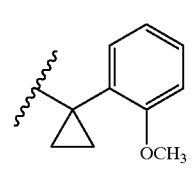 | 3,2 | 1020 (M + 1) |
| 54 | M-8 (a) | H | — | 2 | H | 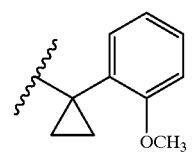 | 3,2 | 1006 (M + 1) |
| 55 | M-8 (a) | NH₂ | — | 2 | CH₃ | 2-methoxybenzyl | 3,2 | 1009 (M + 1) |
| 56 | M-8 (a) | NH₂ | — | 2 | H | 2-methoxybenzyl | 3,2 | 995 (M + 1) |
| 57 | M-8 (a) | NH₂ | — | 2 | CH₃ | 3,5-dimethyl-4-isoxazolylmethyl | 3,2 | 998 (M + 1) |
| 58 | M-8 (a) | NH₂ | — | 2 | H | 2-hydroxybenzyl | 3,2 | 981 (M + 1) |
| 59 | M-8 (a) | NH₂ | — | 2 | CH₃ | 2-hydroxybenzyl | 3,2 | 995 (M + 1) |
| 60 | M-9 | OH | — | 2 | 2,4-dimethoxybenzyl | 2,4-dimethoxybenzyl | 3,2 | 1135 (M) |
| 61 | M-9 | OH | — | 2 | H | 3-(4-chlorophenoxy)benzyl | 3,2 | 1051 (M) |
| 62 | M-9 | 2-(dimethyl-amino)ethoxy | — | 2 | 2,4-dimethoxybenzyl | 2,4-dimethoxybenzyl | 3,2 | 1206 (M) |
| 63 | M-9 | 2-methoxy ethoxymethoxy | — | 3 | 2,4-dimethoxybenzyl | 2,4-dimethoxybenzyl | 3,2 | 1239 (M + 1) |
| 64 | M-9 | OH | — | 3 | 2,4-dimethoxybenzyl | 2,4-dimethoxybenzyl | 3,2 | 1150 (M + 1) |
| 65 | M-10 (a) | — | — | 2 | H | 4-chlorobenzyl | 3,2 | 1008 (M + 1) |
| 66 | M-10 (a) | — | — | 2 | 4-chlorobenzyl | 4-chlorobenzyl | 3,2 | 1132 (M + 1) |
| 67 | M-10 (a) | — | — | 2 | H | 2,3-dimethoxybenzyl | 3,2 | 1034 (M + 1) |
| 68 | M-10 (a) | — | — | 2 | 2,4-dimethoxybenzyl | 2,4-dimethoxybenzyl | 3,2 | 1184 (M + 1) |
| 69 | M-10 (a) | — | — | 2 | H | 2,4-dimethoxybenzyl | 3,2 | 1034 (M + 1) |
| 70 | M-10 (a) | — | — | 2 | 2,4-difluorobenzyl | 2,4-difluorobenzyl | 3,2 | 1136 (M + 1) |
| 71 | M-10 (a) | — | — | 2 | H | 4-pyridylmethyl | 3,2 | 975 (M + 1) |

TABLE 2-continued

| | | | | | | | | |
|---|---|---|---|---|---|---|---|---|
| 72 | M-10 (a) | — | — | 2 | H | 2-methoxybenzoyl | 3,2 | 1019 (M + 1) |
| 73 | M-10 (a) | — | — | 2 | 4-pyridylmethyl | 4-pyridylmethyl | 3,2 | 1066 (M + 1) |
| 74 | M-10 (a) | — | — | 2 | H | 2-methoxybenzyl | 3,2 | 1004 (M + 1) |
| 75 | M-10 (a) | — | — | 2 | H | 2-furylmethyl | 3,2 | 964 (M + 1) |
| 76 | M-10 (a) | — | — | 2 | propyl | 2-methoxybenzyl | 3,2 | 1046 (M + 1) |
| 77 | M-10 (b) | — | — | — | — | 2-methoxybenzyl | 3,2 | 1030 (M + 1) |
| 78 | M-11 | H | H | 2 | 2-methoxybenzyl | 2-methoxybenzyl | 3,2 | 1126 (M + 1) |
| 79 | M-11 | H | H | 2 | H | 3-furylmethyl | 3,2 | 966 (M + 1) |
| 80 | M-11 | H | H | 2 | H | 2-methoxybenzyl | 3,2 | 1006 (M + 1) |
| 81 | M-11 | H | H | 2 | 3-furylmethyl | 3-furylmethyl | 3,2 | 1046 (M + 1) |
| 82 | M-11 | H | H | 2 | H | N-methyl-2-pyrrolylmethyl | 3,2 | 979 (M + 1) |
| 83 | M-11 | H | CH$_3$ | 2 | CH$_3$ | 2-methoxybenzyl | 3,2 | 1034 (M + 1) |
| 84 | M-11 | CH$_3$ | H | 2 | H | 2-methoxybenzyl | 3,2 | 1021 (M + 1) |
| 85 | M-11 | H | H | 2 | H | 3-chloro-2-methoxybenzyl | 3,2 | 1040 (M + 1) |
| 86 | M-11 | H | H | 2 | 3-furylmethyl | 2-methoxybenzyl | 3,2 | 1087 (M + 1) |
| 87 | M-12 | H | H | 2 | 2,4-dimethoxybenzyl | 2,4-dimethoxybenzyl | 3,2 | 1121 (M + 1) |
| 88 | M-12 | H | H | 2 | 4-pyridylmethyl | 4-pyridylmethyl | 3,2 | 1003 (M + 1) |
| 89 | M-12 | H | H | 2 | 2-pyridylmethyl | 2-pyridylmethyl | 3,2 | 1003 (M + 1) |
| 90 | M-12 | H | H | 2 | H | 3-(2,6-dichlorophenyl)-2-propenyl | 3,2 | 1006 (M + 1) |
| 91 | M-12 | H | H | 2 | H | 2,4-dimethoxybenzyl | 3,2 | 971 (M + 1) |
| 92 | M-12 | H | H | 2 | 6,6-dimethyl-2-bicyclo[3.1.1]heptylmethyl | 6,6-dimethyl-2-bicyclo[3.1.1]heptylmethyl | 3,2 | 1095 (M + 1) |
| 93 | M-12 | H | H | 2 | 2-methoxy-4-methylthiobenzyl | 2-methoxy-4-methylthiobenzyl | 3,2 | 1153 (M + 1) |
| 94 | M-12 | H | H | 2 | 2,4-dimethoxybenzyl | 2-methylthiobenzyl | 3,2 | 1107 (M + 1) |
| 95 | M-12 | H | H | 2 | 2,4-dimethoxybenzyl | 2-fluorobenzyl | 3,2 | 1080 (M + 1) |
| 96 | M-12 | H | H | 2 | H | 2,4-bis(difluoromethoxy)benzyl | 3,2 | 1044 (M + 1) |
| 97 | M-12 | H | H | 2 | H | 5-bromo-2-methoxybenzyl | 3,2 | 1021 (M + 1) |
| 98 | M-12 | H | H | 2 | 3-methoxybutyl | 2,4-dimethoxybenzyl | 3,2 | 1058 (M + 1) |
| 99 | M-12 | H | H | 2 | CH$_3$ | 2,4-dimethoxybenzyl | 3,2 | 986 (M + 1) |
| 100 | M-12 | H | H | 2 | 2-methoxybenzyl | 2-methoxybenzyl | 3,2 | 1070 (M + 1) |
| 101 | M-12 | H | H | 2 | 4-(3-(dimethylamino)propoxy)benzyl | 4-(3-(dimethylamino)propoxy)benzyl | 3,2 | 1204 (M + 1) |
| 102 | M-12 | H | H | 2 | H | perfluorophenyl-methyl | 3,2 | 1002 (M + 1) |
| 103 | M-12 | H | H | 2 | H | 3,7,8-tetrahydro-2-naphthylmethyl | 3,2 | 966 (M + 1) |
| 104 | M-12 | H | H | 2 | H | diphenylmethyl | 3,2 | 988 (M + 1) |
| 105 | M-12 | H | H | 2 | 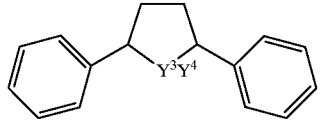 | | 3,2 | 1028 (M + 1) |
| 106 | M-12 | H | H | 2 | H | 3-methoxybenzyl | 3,2 | 980 (M + 1) |
| 107 | M-12 | H | H | 2 | 2-methoxybenzyl | 3-(methylthio)butyl | 3,2 | 1044 (M + 1) |
| 108 | M-12 (9R) | H | H | 2 | 3-methoxybutyl | 2-methoxybenzyl | 3,2 | 1028 (M + 1) |
| 109 | M-12 | H | H | 2 | 2-butenyl | 2-methoxybenzyl | 3,2 | 996 (M + 1) |
| 110 | M-12 | H | H | 2 | 2-methoxyethyl | 2-methoxybenzyl | 3,2 | 1013 (M) |
| 111 | M-12 | H | H | 2 | 3-(methylthio)butyl | 2-methoxy-3-pyridylmethyl | 3,2 | 1045 (M + 1) |
| 112 | M-12 | H | H | 2 | H | 3-furylmethyl | 3,2 | 915 (M + 1) |
| 113 | M-12 | H | H | 2 | 3-methoxybutyl | 2-methoxybenzyl | 3,2 | 1028 (M + 1) |
| 114 | M-12 | H | H | 2 | butyl | 2-methoxybenzyl | 3,2 | 1011 (M) |
| 115 | M-12 | H | H | 2 | 3-methoxybutyl | 5-methyl-2-thiazolylmethyl | 3,2 | 1019 (M + 1) |
| 116 | M-12 (6-MeO) | H | H | 2 | 3-methoxybutyl | 2-methoxybenzyl | 3,2 | 1041 (M) |
| 117 | M-12 (6-MeO) | H | H | 2 | 3-(methylthio)butyl | 2-methoxybenzyl | 3,2 | 1057 (M) |
| 118 (a) | M-12 | H | H | 2 | 3-methoxybutyl | (R)-1-(2-methoxyphenyl)ethyl | 3,2 | 1042 (M + 1) |
| 118 (b) | M-12 | H | H | 2 | 3-methoxybutyl | (S)-1-(2-methoxyphenyl)ethyl | 3,2 | 1042 (M + 1) |

TABLE 2-continued

| | | | | | | | | |
|---|---|---|---|---|---|---|---|---|
| 119 | M-12 | H | H | 2 | 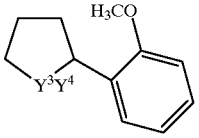 | | 3,2 | 981 (M) |
| 120 (a) | M-12 | H | H | 2 | H | (R)-1-(2-methoxyphenyl)ethyl | 3,2 | 956 (M + 1) |
| 120 (b) | M-12 | H | H | 2 | H | (S)-1-(2-methoxyphenyl)ethyl | 3,2 | 956 (M + 1) |
| 121 | M-12 | H | H | 2 | 3-methoxybutyl | 2,2,2-trifluoro-1-(2-methoxyphenyl)ethyl | 3,2 | 1066 (M + 1) |
| 122 | M-12 | H | H | 2 | tetrahydro-furfuryl | 2-methoxybenzyl | 3,2 | 1026 (M + 1) |
| 123 (a) | M-12 | H | H | 2 | 3-methoxybutyl | (S)-1-(2-methoxyphenyl)ethyl | 3,2 | 1028 (M + 1) |
| 123 (b) | M-12 | H | H | 2 | 3-methoxybutyl | (R)-1-(2-methoxyphenyl)ethyl | 3,2 | 1028 (M + 1) |
| 124 | M-12 | H | H | 2 | 2-methoxypropyl | 2-methoxybenzyl | 3,2 | 1014 (M + 1) |
| 125 (a) | M-12 | H | H | 2 | 2-methoxypropyl | (R)-1-(2-methoxyphenyl)ethyl | 3,2 | 1028 (M + 1) |
| 125 (b) | M-12 | H | H | 2 | 2-methoxypropyl | (S)-1-(2-methoxyphenyl)ethyl | 3,2 | 1028 (M + 1) |
| 126 (a) | M-12 | H | H | 2 | tetrahydro-furfuryl | (R)-1-(2-methoxyphenyl)ethyl | 3,2 | 1040 (M + 1) |
| 126 (b) | M-12 | H | H | 2 | tetrahydro-furfuryl | (S)-1-(2-methoxyphenyl)ethyl | 3,2 | 1040 (M + 1) |
| 127 | M-12 | H | H | 2 | 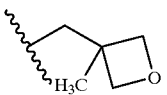 | 2-methoxybenzyl | 3,2 | 1026 (M + 1) |
| 128 | M-12 | H | H | 2 | 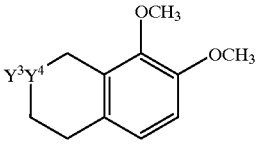 | | 3,2 | 997 (M + 1) |
| 129 | M-12 | H | H | 2 | 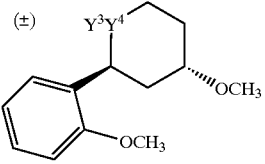 | | 3,2 | 1026 (M + 1) |
| 130 (a) | M-12 | H | H | 2 | tetrahydro-3-furanmethyl | (R)-1-(2-methoxyphenyl)ethyl | 3,2 | 1040 (M + 1) |
| 130 (b) | M-12 | H | H | 2 | tetrahydro-3-furanmethyl | (S)-1-(2-methoxyphenyl)ethyl | 3,2 | 1040 (M + 1) |
| 131 | M-12 | H | H | 2 | tetrahydro-4-pyran | 2-methoxybenzyl | 3,2 | 1026 (M + 1) |
| 132 | M-12 | H | H | 2 | 2-methoxyethyl | 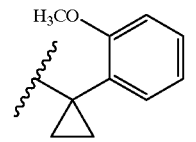 | 3,2 | 1026 (M + 1) |
| 133 | M-12 | H | H | 2 | 3-methoxybutyl | 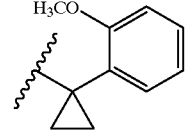 | 3,2 | 1054 (M + 1) |
| 134 | M-12 | H | H | 2 | H | 4-chroman | 3,2 | 954 (M + 1) |
| 135 | M-12 | H | H | 2 | 2-isopropoxyethyl | 2-methoxybenzyl | 3,2 | 1028 (M + 1) |
| 136 | M-12 | H | H | 2 | 2-ethoxyethyl | 2-methoxybenzyl | 3,2 | 1014 (M + 1) |
| 137 | M-12 | H | H | 2 | CH$_3$ | 2-methoxybenzyl | 3,2 | 956 (M + 1) |

TABLE 2-continued

| # | | | | | | | | |
|---|---|---|---|---|---|---|---|---|
| 138 | M-12 | H | H | 2 | ethyl | 2-methoxybenzyl | 3,2 | 970 (M + 1) |
| 139 | M-12 | H | H | 2 | isopropyl | 2-methoxybenzyl | 3,2 | 984 (M + 1) |
| 140 | M-12 | H | H | 2 | propyl | 2-methoxybenzyl | 3,2 | 984 (M + 1) |
| 141 | M-12 | H | H | 2 | cyclopropylmethyl | 2-methoxybenzyl | 3,2 | 996 (M + 1) |
| 142 | M-12 | H | H | 2 | cyclopropyl | 2-methoxybenzyl | 3,2 | 982 (M + 1) |
| 143 (a) | M-12 | H | H | 2 | CH$_3$ | (R)-1-(2-methoxyphenyl)ethyl | 3,2 | 970 (M + 1) |
| 143 (b) | M-12 | H | H | 2 | CH$_3$ | (S)-1-(2-methoxyphenyl)ethyl | 3,2 | 970 (M + 1) |
| 144 (a) | M-12 | H | H | 2 | ethyl | (R)-1-(2-methoxyphenyl)ethyl | 3,2 | 984 (M + 1) |
| 144 (b) | M-12 | H | H | 2 | ethyl | (S)-1-(2-methoxyphenyl)ethyl | 3,2 | 984 (M + 1) |
| 145 (a) | M-12 | H | H | 2 | propyl | (R)-1-(2-methoxyphenyl)ethyl | 3,2 | 998 (M + 1) |
| 145 (b) | M-12 | H | H | 2 | propyl | (S)-1-(2-methoxyphenyl)ethyl | 3,2 | 998 (M + 1) |
| 146 | M-12 | H | H | 2 | H | 1-(2-methoxyphenyl)pentyl | 3,2 | 998 (M + 1) |
| 147 | M-12 | H | H | 2 | ethyl | 1-(2-methoxyphenyl)propyl | 3,2 | 970 (M + 1) |
| 148 | M-12 | H | H | 2 | 4-(dimethylamino)-benzyl | 4-(dimethylamino)-benzyl | 3,2 | 1087 (M + 1) |
| 149 | M-12 | 2-hydroxystyryl | | 2 | 3-methoxybutyl | 2-methoxybenzyl | 3,2 | 1132 (M + 1) |
| 150 | M-12 | CH$_3$ | H | 2 | 2,4-dimethoxybenzyl | 2,4-dimethoxybenzyl | 3,2 | 1136 (M + 1) |
| 151 | M-12 | CH$_3$ | CH$_3$ | 2 | 2,4-dimethoxybenzyl | 2,4-dimethoxybenzyl | 3,2 | 1150 (M + 1) |
| 152 | M-12 | H | propyl | 2 | 2,4-dimethoxybenzyl | 2,4-dimethoxybenzyl | 3,2 | 1164 (M + 1) |
| 153 | M-12 | H | amidino | 2 | 2,4-dimethoxybenzyl | 2,4-dimethoxybenzyl | 3,2 | 1164 (M + 1) |
| 154 | M-12 | isobutenyl | | 2 | 2-(difluoromethoxy)-benzyl | 2-(difluoromethoxy)-benzyl | 3,2 | 1084 (M + 1) |
| 155 | M-12 | 2-hydroxystyryl | | 2 | 2,4-dimethoxybenzyl | 2,4-dimethoxybenzyl | 3,2 | 1226 (M + 1) |
| 156 | M-12 (9R) | CH$_3$ | CH$_3$ | 2 | H | 2-methoxybenzyl | 3,2 | 984 (M + 1) |
| 157 | M-12 | H | formyl | 2 | 3-methoxybutyl | 2-methoxybenzyl | 3,2 | 1056 (M + 1) |
| 158 (a) | M-12 | H | propyl | 2 | 3-methoxybutyl | (R)-1-(2-methoxyphenyl)ethyl | 3,2 | 1084 (M + 1) |
| 158 (b) | M-12 | H | propyl | 2 | 3-methoxybutyl | (S)-1-(2-methoxyphenyl)ethyl | 3,2 | 1084 (M + 1) |
| 159 (a) | M-12 | H | butyl | 2 | 3-methoxybutyl | (R)-1-(2-methoxyphenyl)ethyl | 3,2 | 1098 (M + 1) |
| 159 (b) | M-12 | H | butyl | 2 | 3-methoxybutyl | (S)-1-(2-methoxyphenyl)ethyl | 3,2 | 1098 (M + 1) |
| 160 | M-12 | 2-hydroxystyryl | | 2 | tetrahydro-4-pyranyl | 2-methoxybenzyl | 3,2 | 1130 (M + 1) |

TABLE 2-continued

| | | | | | | | | |
|---|---|---|---|---|---|---|---|---|
| 161 | M-12 | (2-fluoro-6-hydroxyphenyl vinyl group) | | 2 | 2,4-dimethoxybenzyl | 2,4-dimethoxybenzyl | 3,2 | 1245 (M + 1) |
| 162 | M-6 | CH₃ | — | 0 | H | 3-(2-methoxyphenyl)propyl | 3,2 | 954 (M) |
| 163 | M-6 | CH₃ | — | 0 | H | H | 3,2 | 806 (M) |
| 164 | M-8 (a) | H | — | 0 | H | H | 3,2 | 831 (M) |
| 165 | M-6 | H | — | 0 | H | 3-furylmethyl | 3,2 | 887 (M + 1) |
| 166 | M-8 (a) | H | — | 0 | H | 3-(2-methoxyphenyl)propyl | 3,2 | 979 (M) |
| 167 | M-8 (a) | H | — | 0 | H | 2-methoxybenzyl | 3,2 | 952 (M + 1) |
| 168 | M-8 (a) | H | — | 0 | H | 3-furylmethyl | 3,2 | 912 (M + 1) |
| 169 | M-12 | H | H | 2 | 2,4-dimethoxybenzyl | 2,4-dimethoxybenzyl | 3,2 | 1148 (M + 1) |
| 170 | M-7 | H | — | 2 | 2-methoxyethyl | 2-methoxybenzyl | 3,2 | 1025 (M + 1) |
| 171 | M-7 | H | — | 2 | 2-(2-methoxyethoxy)ethyl | 2-methoxybenzyl | 3,2 | 1069 (M + 1) |
| 172 | M-7 | H | — | 2 | 2-pyridylmethyl | 2-methoxybenzyl | 3,2 | 1058 (M + 1) |
| 173 | M-7 | CH₃ | — | 2 | 2-methoxyethyl | 2-methoxyethyl | 3,2 | 977 (M + 1) |
| 174 | M-7 | H | — | 2 | 2-methoxyethyl | 3-methoxybutyl | 3,2 | 992 (M + 1) |
| 175 | M-7 | H | — | 2 | 3-methoxybutyl | 2,4-dimethoxybenzyl | 3,2 | 1083 (M + 1) |
| 176 | M-7 | H | — | 2 | ethyl | 2,4-dimethoxybenzyl | 3,2 | 1025 (M + 1) |
| 177 | M-7 | CH₃ | — | 2 | isobutyl | 2-methoxybenzyl | 3,2 | 1037 (M + 1) |
| 178 | M-13 | H | H | 2 | 3-methoxybutyl | 2-methoxybenzyl | 3,2 | 1054 (M + 1) |
| 179 | M-13 | H | H | 2 | H | 2-methoxybenzyl | 3,2 | 981 (M + 1) |
| 180 | M-14 | H | CH₃ | 2 | 2,4-dimethoxybenzyl | 2,4-dimethoxybenzyl | 3,2 | 1062 (M + 1) |
| 181 | M-14 | propyl | H | 2 | 2,4-dimethoxybenzyl | 2,4-dimethoxybenzyl | 3,2 | 1077 (M + 1) |
| 182 | M-14 | H | 2-methoxy propyl | 2 | 2,4-dimethoxybenzyl | 2,4-dimethoxybenzyl | 3,2 | 1207 (M + 1) |
| 183 | M-14 | H | 2-methoxy ethoxymethyl | 2 | 2,4-dimethoxybenzyl | 2,4-dimethoxybenzyl | 3,2 | 1223 (M + 1) |
| 184 | M-15 (a) | CH₃ | — | 3 | 2,4-dimethoxybenzyl | 2,4-dimethoxybenzyl | 3,2 | 1150 (M + 1) |
| 185 | M-15 (a) | CH₃ | — | 3 | H | 2,4-dimethoxybenzyl | 3,2 | 1000 (M + 1) |
| 186 | M-15 (a) | H | — | 3 | 2,4-dimethoxybenzyl | 2,4-dimethoxybenzyl | 3,2 | 1136 (M + 1) |
| 187 | M-15 (a) | CH₃ | — | 2 | H | 4-(4-chlorophenoxy)-2-methoxybenzyl | 3,2 | 1053 (M + 1) |
| 188 | M-15 (a) | CH₃ | — | 2 | H | 2-methoxybenzyl | 3,2 | 996 (M + 1) |
| 189 | M-15 (a) | CH₃ | — | 2 | 3-methoxybutyl | 2-methoxybenzyl | 3,2 | 1042 (M + 1) |
| 190 | M-15 (a) | CH₃ | — | 2 | H | 1-(2-methoxyphenyl)cyclopropyl | 3,2 | 982 (M + 1) |
| 191 | M-15 (a) | CH₃ | — | 2 | CH₃ | 1-(2-methoxyphenyl)cyclopropyl | 3,2 | 996 (M + 1) |
| 192 (a) | M-15 (a) | CH₃ | — | 2 | 3-methoxybutyl | (R)-1-(2-methoxyphenyl)ethyl | 3,2 | 1056 (M + 1) |
| 192 (b) | M-15 (a) | CH₃ | — | 2 | 3-methoxybutyl | (S)-1-(2-methoxyphenyl)ethyl | 3,2 | 1056 (M + 1) |
| 193 (a) | M-15 (a) | CH₃ | — | 2 | tetrahydrofurfuryl | (R)-1-(2-methoxyphenyl)ethyl | 3,2 | 1054 (M + 1) |
| 193 (b) | M-15 (a) | CH₃ | — | 2 | tetrahydrofurfuryl | (S)-1-(2-methoxyphenyl)ethyl | 3,2 | 1054 (M + 1) |
| 194 | M-15 (a) | H | — | 2 | H | 2-methoxybenzyl | 3,2 | 942 (M + 1) |
| 195 | M-15 (a) | H | — | 2 | CH₃ | 2-methoxybenzyl | 3,2 | 956 (M) |
| 196 | M-15 (a) | H | — | 2 | 2-methoxyethyl | 2-methoxybenzyl | 3,2 | 1000 (M + 1) |
| 197 | M-15 (a) | H | — | 2 | 3-methoxybutyl | 2-methoxybenzyl | 3,2 | 1028 (M + 1) |
| 198 | M-15 (a) | H | — | 2 | ethyl | 2-methoxybenzyl | 3,2 | 968 (M + 1) |
| 199 | M-15 (a) | CH₃ | — | 2 | ethyl | 2-methoxybenzyl | 3,2 | 984 (M + 1) |
| 200 | M-15 (a) | H | — | 2 | propyl | 2-methoxybenzyl | 3,2 | 984 (M + 1) |
| 201 | M-15 (a) | H | — | 2 | isopropyl | 2-methoxybenzyl | 3,2 | 984 (M + 1) |
| 202 | M-15 (b) | CH₃ | — | 2 | — | 1-(2-methoxyphenyl)ethyl | 3,2 | 1039 (M + 1) |
| 203 | M-15 (b) | CH₃ | — | 1 | — | 2-methoxybenzyl | 3,2 | 928 (M + 1) |

TABLE 2-continued

| | | | | | | | | |
|---|---|---|---|---|---|---|---|---|
| 204 | M-15 (a) | CH₃ | — | 2 | isopropyl | 2-methoxybenzyl | 3,2 | 996 (M + 1) |
| 205 | M-15 (a) | CH₃ | — | 2 | H | 1-(2-methoxyphenyl)pentyl | 3,2 | 1012 (M + 1) |
| 206 | M-15 (a) | CH₃ | — | 2 | isopropyl | 2-methoxybenzyl | 3,2 | 998 (M + 1) |
| 207 | M-15 (a) | CH₃ | — | 2 | H | 1-(2-hydroxyphenyl)ethyl | 3,2 | 956 (M + 1) |
| 208 | M-15 (a) | CH₃ | — | 2 | propyl | 2-hydroxybenzyl | 3,2 | 984 (M + 1) |
| 209 | M-15 (a) | CH₃ | — | 2 | ethyl | 2-hydroxybenzyl | 3,2 | 970 (M + 1) |
| 210 | M-15 (a) | CH₃ | — | 2 | CH₃ | 1-(2-hydroxyphenyl)ethyl | 3,2 | 970 (M + 1) |
| 211 | M-15 (a) | CH₃ | — | 2 | H | 1-(2-hydroxyphenyl)propyl | 3,2 | 970 (M + 1) |
| 212 | M-15 (a) | CH₃ | — | 2 | H | 1-(2-methoxyphenyl)propyl | 3,2 | 984 (M + 1) |
| 213 | M-15 (a) | CH₃ | — | 2 | CH₃ | 1-(2-hydroxyphenyl)propyl | 3,2 | 984 (M + 1) |
| 214 | M-15 (a) | CH₃ | — | 2 | CH₃ | 1-(2-methoxyphenyl)propyl | 3,2 | 998 (M + 1) |
| 215 | M-15 (a) | CH₃ | — | 2 | H | 2-(2-methoxyphenoxy)ethyl | 3,2 | 986 (M + 1) |
| 216 | M-15 (a) | CH₃ | — | 3 | CH₃ | (R)-1-(2-methoxyphenyl)ethyl | 3,2 | 998 (M + 1) |
| 216 | M-15 (a) | CH₃ | — | 3 | CH₃ | (S)-1-(2-methoxyphenyl)ethyl | 3,2 | 998 (M + 1) |
| 217 | M-15 (a) | CH₃ | — | 2 | H | ethyl | 3,2 | 864 (M + 1) |
| 218 | M-15 (a) | CH₃ | — | 3 | H | 1-(2-hydroxyphenyl)ethyl | 3,2 | 970 (M + 1) |
| 219 | M-15 (a) | CH₃ | — | 3 | ethyl | 1-(2-hydroxyphenyl)ethyl | 3,2 | 998 (M + 1) |
| 220 | M-15 (a) | CH₃ | — | 3 | CH₃ | 1-(2-hydroxyphenyl)ethyl | 3,2 | 984 (M + 1) |
| 221 | M-16 | CH₃ | H | — | 3-methoxybutyl | 2-methoxybenzyl | 3,2 | 1042 (M + 1) |
| 222 | M-16 | CH₃ | CH₃ | — | 3-methoxybutyl | 2-methoxybenzyl | 3,2 | 1056 (M + 1) |
| 223 | M-16 | H | 2-methoxybenzyl | — | H | H | 3,2 | 942 (M + 1) |
| 224 | M-16 | | 2-methoxybenzyl | — | CH₃ | CH₃ | 3,2 | 970 (M + 1) |
| 225 | M-17 | CH₃ | CH₃ | — | H | 2-hydroxybenzyl | 3,2 | 994 (M + 1) |
| 226 | M-17 | CH₃ | CH₃ | — | CH₃ | 2-hydroxybenzyl | 3,2 | 1008 (M + 1) |
| 227 | M-17 | CH₃ | H | — | H | 2-hydroxybenzyl | 3,2 | 980 (M + 1) |
| 228 | M-17 | CH₃ | H | — | CH₃ | 2-hydroxybenzyl | 3,2 | 994 (M + 1) |
| 229 | M-17 | H | 2-methoxybenzyl | — | H | H | 3,2 | 980 (M + 1) |
| 230 | M-18 | — | — | — | 2,4-dimethoxybenzyl | 3-(trifluoromethyl)-benzyl | 4 | 1158 (M + 1) |
| 231 | M-18 | — | — | — | 2,4-dimethoxybenzyl | 2,4-difluorobenzyl | 4 | 1112 (M + 1) |
| 232 | M-18 | — | — | 0 | 2,4-dimethoxybenzyl | 4-cyanobenzyl | 4 | 1101 (M + 1) |
| 233 | M-8 (a) | H | — | 2 | H | 2-methoxybenzyl | 3,2 | 980 (M + 1) |
| 234 | M-8 (b) | H | — | — | — | 2-methoxybenzyl | 3,2 | 1005 (M + 1) |
| 235 | M-12 | H | H | 2 | 2-propenyl | (R)-1-(2-methoxyphenyl)ethyl | 3,2 | 996 (M + 1) |
| 235 | M-12 | H | H | 2 | 2-propenyl | (S)-1-(2-methoxyphenyl)ethyl | 3,2 | 996 (M + 1) |
| 236 | M-12 | H | H | 2 | H | 1-(2-methoxyphenyl)propyl | 3,2 | 970 (M + 1) |
| 237 | M-12 | ![HO-phenyl-vinyl] | | 2 | isopropyl | 2-methoxybenzyl | 3,2 | 1088 (M + 1) |
| 238 | M-12 | ![HO-phenyl-vinyl] | | 2 | ethyl | 2-methoxybenzyl | 3,2 | 1074 (M + 1) |
| 239 | M-12 | ![CH₃ C=C(OCH₂CH₃)C(=O)] | | 2 | isopropyl | 2-methoxybenzyl | 3,2 | 1068 (M + 1) |
| 240 | M-12 | H | H | 2 | allyl | 2-methoxybenzyl | 3,2 | 982 (M + 1) |
| 241 | M-12 | H | H | 2 | allyl | 2,4-dimethoxybenzyl | 3,2 | 1012 (M + 1) |

TABLE 2-continued

| | | | | | | | | |
|---|---|---|---|---|---|---|---|---|
| 242 | M-12 | H | H | 2 | allyl | (R)-1-(2-methoxyphenyl)ethyl | 3,2 | 996 (M + 1) |
| 243 | M-12 | H | H | 2 | allyl | (S)-1-(2-methoxyphenyl)ethyl | 3,2 | 996 (M + 1) |
| 244 | M-12 | H | H | 2 | allyl | (R)-1-(2,4-dimethoxyphenyl)ethyl | 3,2 | 1026 (M + 1) |
| 245 | M-12 | H | H | 2 | allyl | (S)-1-(2,4-dimethoxyphenyl)ethyl | 3,2 | 1026 (M + 1) |
| 246 | M-12 | H | H | 2 | propargyl | 2-methoxybenzyl | 3,2 | 980 (M + 1) |
| 247 | M-12 | H | H | 2 | propargyl | 2,4-dimethoxybenzyl | 3,2 | 1010 (M + 1) |
| 248 | M-12 | H | H | 2 | propargyl | (R)-1-(2-methoxyphenyl)ethyl | 3,2 | 994 (M + 1) |
| 249 | M-12 | H | H | 2 | propargyl | (S)-1-(2-methoxyphenyl)ethyl | 3,2 | 994 (M + 1) |
| 250 | M-12 | H | H | 2 | propargyl | (R)-1-(2,4-dimethoxyphenyl)ethyl | 3,2 | 1024 (M + 1) |
| 251 | M-12 | H | H | 2 | propargyl | (S)-1-(2,4-dimethoxyphenyl)ethyl | 3,2 | 1024 (M + 1) |
| 252 | M-12 | H | H | 2 | isopropyl | (R)-1-(2-methoxyphenyl)ethyl | 3,2 | 998 (M + 1) |
| 253 | M-12 | H | H | 2 | isopropyl | (S)-1-(2-methoxyphenyl)ethyl | 3,2 | 998 (M + 1) |
| 254 | M-12 | H | H | 2 | isopropyl | (R)-1-(2,4-dimethoxyphenyl)ethyl | 3,2 | 1028 (M + 1) |
| 255 | M-12 | H | H | 2 | isopropyl | (S)-1-(2,4-dimethoxyphenyl)ethyl | 3,2 | 1028 (M + 1) |
| 256 | M-12 | H | H | 2 | propyl | (R)-1-(2,4-dimethoxyphenyl)ethyl | 3,2 | 1028 (M + 1) |
| 257 | M-12 | H | H | 2 | propyl | (S)-1-(2,4-dimethoxyphenyl)ethyl | 3,2 | 1028 (M + 1) |
| 258 | M-12 | H | H | 2 | methyl | 3-(2,5-dimethyl)-thiophenyl | 3,2 | 973 (M + 1) |
| 259 | M-12 | H | H | 2 | methyl | 3-(2,5-dichloro)-thiophenyl | 3,2 | 1013 (M) |

We claim:

1. A compound of the formula

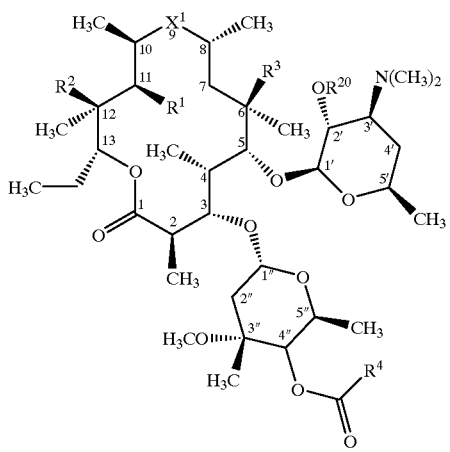

and pharmaceutically acceptable salts thereof wherein:

$X^1$ is —$CH_2R^9$— or —$NR^9CH_2$—, wherein the first dash of either of the foregoing $X^1$ groups is attached to the C-10 carbon of the compound of formula 1 and the last dash of each group is attached to the C8 carbon of the compound of formula 1;

$R^1$ and $R^2$ are each independently OH;

or $R^2$ is O and $R^1$ is $X^2$, and they are taken together as follows:

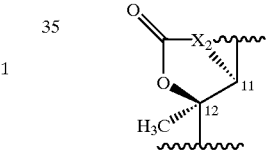

wherein $X^2$ is O, —$N(R^9)$—, or —$N(NR^9R^{10})$—;

[or $R^1$ is oxo, OH, or —$NR^9R^{10}$, $R^2$ is O and $X^1$ is —CH(—O)—, and $R^2$ and $X^1$ are taken together as follows:

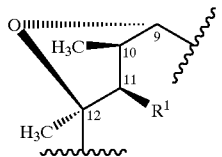

or $R^1$ is N, $R^2$ is O, $X^1$ is —C(=N)— or —CH(—$NR^9$)—, and $R^1$ is taken together wit both $R^2$ and $X^1$ as follows:

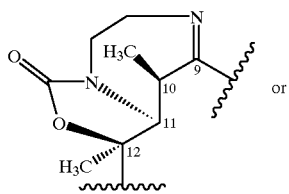

or

-continued

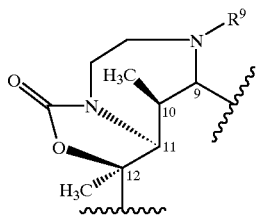

or R¹ is O and X¹ is —C(—NR⁹)—, and they are taken together as follows:

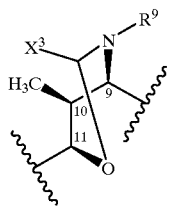

wherein X³ is H, C₁–C₆ alkyl, or —(CH₂)ₘO(C₁–C₆ akyl) wherein m is an integer ranging from 1 to 4 and the alkyl moieties of the foregoing X³ groups are optionally substituted by 1 or 2 substituents independently selected from halo, —NR⁹R¹⁰ and —OR⁹;]

R³ is hydroxy or methoxy;

R⁴ is —(CH₂)ₙNR⁸R¹⁵ wherein n is an integer ranging from 0 to 6 and said R⁴ group is optionally substituted by 1 to 3 R¹⁶ groups, with the proviso that n is not 0 where R⁸ is —C(O)(C₁–C₁₀ alkyl), —C(O)(CH₂)ₜ (C₆–C₁₀ aryl), or —C(O)(CH₂)ₜ(4–10 membered heterocyclic);

[R⁵ is hydroxy, C₁–C₆ allkyl, C₁–C₆ alkoxy, —(CH₂)ₘ (C₆–C₁₀ aryl), —CH₂)ₘ(4–10 membered heterocyclic), or —(CH₂)ₘO(CH₂)ᵤOR⁹, wherein m is an integer ranging fom 0 to 4 and z is an integer ranging from 1 to 6, and the foregoing R⁵ groups, except hydroxy, are optionally substituted by 1 to 3 R¹⁶ groups;]

each R⁶ and R⁷ is independently H, OR⁹, C₁–C₆ alkyl, —(CH₂)ₘ(C₆–C₁₀ aryl), or —(CH₂)ₘ(4–10 membered heterocyclic), wherein m is an integer ranging from 0 to 4, with the proviso that where R⁶ and R⁷ are both attached to the same nitrogen as —NR⁶R⁷, then R⁶ and R⁷ are not both —OR⁹;

R⁸ is C₁–C₁₀ alkyl, —C(O)(C₁–C₁₀ akly), —(CH₂)_qCR¹¹R¹²—(CH₂)ᵣNR¹³R¹⁴ wherein q and r are each independently an integer ranging from 0 to 4 except that q and r are not both 0, —(CH₂)ₜ(C₆–C₁₀ aryl), —(CH₂)ₜ(4–10 membered heterocyclic), —(O)(CH₂)ₜ (C₆–C₁₀ aryl), —(C(O)(CH₂)ₜ(C₆–C₁₀ aryl), —C(O)(CH₂)ₜO(CH₂)ₜ(4–10 membered heterocyclic), —SO(CH₂)ⱼ(C₆–C₁₀ aryl), or —SO₂(CH₂)ⱼ(4–10 membered heterocyclic), wherein j is an integer ranging from 0 to 2, t is an integer raging from 0 to 5, the —(CH₂)ₜ moieties of the foregoing R⁸ groups optionally include a carbon-carbn double or triple bond where t is an integer betwee 2 and 5, and the foregoing R⁸ groups are optionally substituted by 1 to 3 R¹⁶ groups;

or R¹⁵ and R⁸ may be taken together with the nitrogen to which each is attached to form a 4–10 membered saturated rnonocyclic or polycyclic saturated ring or a 5–10 membered heteroaryl ring, wherein said saturated and heteroaryl rings optionally include 1 or 2 heteroatoms selected from O, S and —N(R⁶)— in addition to the nitrogen to which R¹⁵ and R⁸ are attached, said —N(R⁶)— is optionally =N— or —N= where R¹⁵ and R⁸ are taken together as said heteroaryl group, said saturated ring optionally may be partially unsaturated by including 1 or 2 carbon-carbon double bonds, and said saturated and heteroaryl rings, including the R⁶ group of said —N(R⁶)—, are optionally substituted by 1 to 3 R¹⁶ groups;

or R¹⁵ and R⁸ may be taken together with the nitrogen to which each is attached to form a polycyclic moiety of the formula

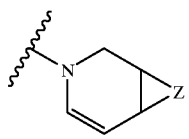

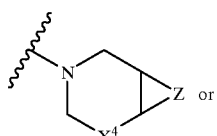

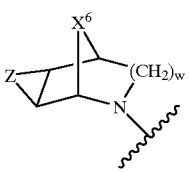

wherein v is 0 or 1, X⁴ is —C(O)—, —CH(OH)—, —(CH₂)ₘ—, —N(R⁶)(CH₂)ₘ, —(CH₂)ₘN(R⁶)— or —(CH₂)ₘO— wherein m is an integer ranging ftom 0 to 2, and X⁶ is —(CH₂)ᵥᵥ— wherein w is 1 or 2, —CH₂O—, —OCH₂—, —CH₂N(R⁹)—, or —N(R⁹) CH₂—;

the  Z portion of groups 2, 3, and 4 is

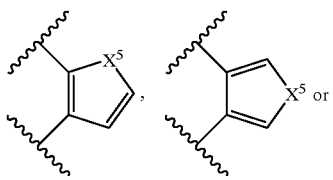

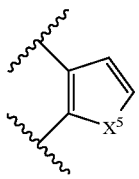

wherein X⁵ is —CH=CH—, —S—, or —N(R⁶)—, and the above groups of formulas 2, 3, and 4, including the Z portions of said groups, are optionally substituted by 1 to 3 $R^{16}$ groups; each $R^9$ and $R^{10}$ is independently H or $C_1$–$C_6$ alky;

each $R^{11}$, $R^{12}$, $R^{13}$ and $R^{14}$ is independently selected from H, $C_1$–$C_{10}$ alkyl, $C_1$–$C_{10}$ alkanoyl, —$(CH_2)_m(C_6$–$C_{10}$ aryl), —$(O)(CH_2)_m(C_6$–$C_{10}$ aryl), —$(CH_2)_m(4$–$10$ membered heterocyclic), and —$C(O)(CH_2)_m(4$–$10$ membered heterocyclic), wherein m is an integer ranging from 0 to 4, and wherein the foregoing $R^{11}$, $R^{12}$, $R^{13}$ and $R^{14}$ groups, except H, are optionally substituted by 1 to 3 $R^{16}$ groups;

or $R^{11}$ and $R^{13}$ are taken together to form —$(CH_2)_p$— wherein p is an integer ranging from 0 to 3 and r+p equals at least 2, such that a 4–9 membered saturated ring is formed that optionally may be partially unsatated by including 1 or 2 carbon-carbon double bonds;

or $R^{13}$ and $R^{14}$ are taken together with the nitrogen to which each is attached to form a 4–10 membered monocyclic or polycyclic saturated ring or a 5–10 membered heteroaryl ring, wherein said saturated and heteroaryl rings optionally include 1 or 2 heteratpms selected from O, S and —$N(R^6)$—, in addition to the nitrogen to which $R^{13}$ and $R^{14}$ are attached, said —$N(^6)$— is optionally =N— or —N= where $R^{13}$ and $R^{14}$ are taken together as said heteroaryl group, said saturated ring optionally may be partially unsaturated by including 1 or 2 carbon-carbon double bonds, and said saturated and heteroaryl rings, including the $R^6$ group of said —$N(R^6)$—, are optionally substituted by 1 to 3 $R^{16}$ groups;

or $R^{13}$ and $R^{14}$ are taken together to form =C(—$NR^9R^6$)$NR^{10}R^7$;

or $R^{13}$ is H and $R^{14}$ is —C(=$NR^6$)$NR^9R^7$;

$R^{15}$ is H or $C_1$–$C_{10}$ allyl, wherein the alkyl is optionally substituted by 1 to 3 $R^{16}$ groups;

each $R^{16}$ is independently selected from halo, cyano, nitro, trifluoromethyl, azido, —$C(O)R^{17}$, —$C(O)OR^{17}$, —$OC(O)R^{17}$, —$OC(O)OR^{17}$, —$NR^6C(O)R^7$, —$C(O)NR^6R^7$, —$NR^6R^7$, hydroxy, $C_1$–$C_6$ alkyl, —$S(O)_j(C_1$–$C_6$ alkyl) wherein j is an integer ranging from 0 to 2, $C_1$–$C_6$ alkoxy, —$(CH_2)_m(C_6$–$C_{10}$ aryl), and —$(CH_2)_m(C_5$–$C_{10}$ mebeted heteroaxyl), wherein m is a integer ranging from 0 to 4, said alkoxy group is optionally substituted by 1 to 3 groups selected from —$NR^9R^{10}$, halo, and —$OR^9$, and said aryl and heteroaryl substituents are optionally substituted by 1 to 5 substituents independently selected from halo, cyano, nitro, trifluoromethyl, azdo, —$C(O)R^{17}$, —$C(O)OR^{17}$, —$CO(O)OR^{17}$, —$OC(O)OR^{17}$, —$NR^6C(O)R^7$, —$C(O)NR^6R^7$, —$NR^6R^7$, hydroxy, $C_1$–$C_6$ alkyl, and $Cl$-$C_6$ alkoxy;

each $R^{17}$ is independently selected from H, $C_1$–$C_{10}$ alkyl, —$(CH_2)_m(C_6$–$C_{10}$ aryl), and —$(CH_2)_m(4$–$10$ membered heteroaryl), wherein m is an integer ranging from 0 to 4;

[$R^{18}$ and $R^{19}$ are each independently selected from H, $C_1$–$C_6$ alkyl, —$C(=NR^5)NR^9R^{10}$, and —$C(O)R^9$, or $R^{18}$ and $R^{19}$ are taken together to form =$CH(CR^9R^{10})_m(4$–$10$ aryl), =$CH(CR^9R^{10})_m(4$–$10$ membered heterocyclic), =$CR^9R^{10}$, or =$C(R^9)C(O)OR^9$, wherein m is an integer ranging from 0 to 4, and wherein the alkyl, aryl and heterocyclic moieties of the foregoing $R^{18}$ and $R^{19}$ groups are optionally substituted by 1 to 3 $R^{16}$ groups;]

$R^{20}$ is H or —$C(O)R^9$.

2. The compound of claim 1 wherein $X^1$ is —$N(CH_3)CH_2$—, $R^1$ and $R^2$ are OH, $R^4$ is —$(CH_2)_nNR^8R^{15}$ wherein n is an integer ranging from 0 to 3, $R^{15}$ is H or methyl, and $R^8$ is —$(CH_2)_qCR^{11}R^{12}(CH_2)_nNR^{13}R^{14}$ wherein q is 1 and r is 0, and $R^{11}$, $R^{12}$, $R^{13}$ and $R^{14}$ are as defined above.

3. The compound of claim 1 wherein $R^4$ is —$(CH_2)_nNR^8R^{15}$ wherein $R^8$ and $R^{15}$ are taken together to form a 4–10 membered saturated ring that optionally includes an additional heteroatom moiety selected from O, S, and —$N(R^6)$—, wherein said ring is optionally substituted by 1 to 3 $R^{16}$ groups.

4. The compound of claim 1 selected from the group consisting of:

[4"-O-[2-(N,N-bis-2,4,-dimethoxybenzyl)aminoethyl]aminocarbonyl-9-deoxo-9-imino-11-deoxy-11-amino-9N,11N-ethylene 6-O-methyl-erythromycin, 11,12-cyclic carbamate;

4"-O-[2-(N,N-bis-2,4-dimethoxybenzyl)aminoethyl] aminocarbonyl erythromycylamine;

4"-O-[2-(N-3-methoxybutyl-N-2-methoxybenzyl) aminoethyl]aminocarbonyl erythromycylamine;

4"-O-[2-(N-2-methoxybenzyl)aminoethyl] aminocarbonyl-11-deoxy-11-amino 6-O-methyl-erythromycin, 11,12-cyclic carbamate;

4"-O-[2-(N-3-furylmethyl)aminoethyl]aminocarbonyl-11-deoxy- 11-amino 6-O-methyl-erythromycin clarithromycin, 11,12-cyclic carbamate;

4"-O-[2-(N-3-methoxybutyl-N-α-methyl-2-methoxybenzyl)aminoethyl]aminocarbonyl erythromycylamine;

4"-O-{2-[2-(2-methoxyphenyl)-pyrrolin-1-yl]ethyl}aminocarbonyl erythromycylamine;

4"-O-[2-(N-2-tetrahydrofurylmethyl-N-α-methyl-2 methoxybenzyl)aminoethyl]aminocarbonyl erythromycylamine;

4"-O-[2-(N-tetrahydropyran-4-yl-N-2-methoxybenzyl) aminoethyl]aminocarbonyl erythromycylamine;

4"-O-{2-[N-(2-isopropyloxy)ethyl-N-2-methoxybenzyl] aminoethyl}aminocarbonyl erythromycylamine;

4"-O-{2-[N-(2-ethoxy)ethyl-N-2-methoxybenzyl] aminoethyl} aminocarbonyl erythromycylamine;

4"-O-[2-(N-ethyl-N-2-methoxybenzyl)aminoethyl] aminocarbonyl erythromycylamine;

4"-O-[2-(N-isopropyl-N-2-methoxybenzyl)aminoethyl] aminocarbonyl erythromycylamine;

4"-O-[2-(N-propyl-N-2-methoxybenzyl)aminoethyl] aminocarbonyl erythromycylamine;

4"-O-[2-(N-cyclopropylmethyl-N-2-methyoxybenzyl) aminoethyl]aminocarbonyl erythromycylamine;

4"-O-[2-(N-methyl-N-α-methyl-2-methoxybenzyl) amioethyl]aminocarbonyl erythromycylamine;

4"-O-[2-(N-ethyl-N-α-methyl-2-methoxybenzyl) aminoethyl]aminocarbonyl erythromycylamine;

4"-O-[2-(N-propyl-N-α-methyl-2-methoxybenzyl) aminoethyl]aminocarbonyl erythromycylamine;]

4"-O-[2-(N-α-methyl-2-methoxybenzyl)aminoethyl] aminocarbonyl azithromycin; and

[4'-O-[2-(N-isopropyl-N-2-methoxybenzyl)arninoethyl] aminocarbonyl erythromycylamine, methyl pyruvate imine;

4"-O-[2-(N-allyl-N-α-methyl-2-methoxybenzyl) aminoethyl]aminocarbonyl erythromycylamine;

4"-O-[2-(N-3-methoxybutyl-N-3-ethyl-5-methylisoxazol-4-ylmethyl)aminoethyl]aminocarbonyl 6-O-methyl-erythromycin;

4"-O-[2-(N-3-methoxybutyl-N-3,5-dimethylisoxazol-4-ylmethyl)aminoethyl]aminocarbonyl erythromycylamine;

4"-O-[2-(N-methyl-N-3,5-dimethylisoxazol-4-ylmethyl) aminoethyl]aminocarbonyl-11-deoxy-11-amino 6-O-methyl-erythromycin, 11,12-cyclic carbamate;

4"-O-[2-(N-methyl-N-3,5-dimethylisoxazol-4-ylmethyl) aminoethyl]aminocarbonyl 6-O-methyl-erythromycin;

4"-O-[2-(N-3,5-dimethylisoxazol-4-ylmethyl) aminoethyl]aminocarbonyl 6-O-methyl-erythromycin;

4"-O-[2-(N-2-methoxybenzyl)aminoethyl] aminocarbonyl-11-deoxy-11-amino 6-O-methyl-erythromycin, 11,12-cyclic carbamate;

4"-O-[2-N-α-butyl-2-methoxybenzyl)aminoethyl] aminocarbonyl-11-deoxy-11-amino 6-O-methyl-erythromycin, 11,12-cyclic carbamate;]

4"-O-[2-(N-methyl-N-α-ethyl-2-methoxybenzyl) aminoethyl]aminocarbonyl azithromycin;

[4"-O-[2-(N-2-methoxy-5-isopropylbenzyl)aminoethyl] aminocarbonyl-11-deoxy-11-amino 6-O-methyl-erythromycin, 11,12-cyclic carbamate;

4"-O-[4-(benzo[d]isoxazol-3-yl)-piperazin]carbonyl-11-deoxy-11-amino 6-O-methyl-erthromycin, 11,12-cyclic carbamate;

4"-O-[2-(N-chroman-4-yl)aminoethyl]aminocarbonyl-11-deoxy-11-amino 6-O-methyl-erythromycin, 11,12-cyclic carbamate;

4"-O-[2-(N-propryl-N-α-methyl-2,4-dimethoxybenzyl) aminoethyl]aminocarbonyl erythromycylamine;

4"-O-[2-(N-ethyl-N-α-methyl-2-methoxybenzyl)amino] butyryl erythromycylamine;

4"-O-[2-(N-3-methoxybutyl-N-3-methoxypyridin-4-ylmethyl)aminoethyl]aminocarbonyl-6-O-methyl erythromycylamine;

4"-O-[2-(N-methyl-N-α-methyl-2,5-dichloro-thiophen-3-ylmethyl)aminoethyl]aminocarbonyl-6-O-methyl erythromycylamine;

4"-O-[2-(N-methyl-N-α-methyl-2,5-dimethyl-thiophen-3-ylmethyl)aminoethyl]aminocarbonyl-6-O-methyl erythromycylamine;]

and pharmaceutically acceptable salts thereof.

5. A pharmaceutical composition for the treatment of a disorder selected from a bacterial infection, a protozoal infection, and a disorder related to a bacterial infection or protozoal infection in a mammal, fish, or bird which comprises a therapeutically effective amount of a compound of claim 1 and a pharmaceutically acceptable carrier.

6. The pharmaceutical composition of claim 5 wherein said disorder is pneumonia, otitis media, sinusitus, bronchitis, tonsillitis, or mastoiditis related to infection by *Streptococcus pneumoniae, Haemophilus influenzae, Moraxella catarrhalis, Staphylococcus aureus,* or *Peptostreptococcus spp.*; pharyngitis, rheumatic fever, or glomerulonephritis related to infection by *Streptococcus pyogenes*, Groups C and G streptococci, *Clostridium diptheriae,* or *Actinobacillus haemolyticum*; a respiratory tract infections related to infection by *Mycoplasma pneumoniae, Legionella pneumophila, Streptococcus pneumoniae, Haemophilus influenzae,* or *Chiamydia pneumoniae*; uncomplicated skin or soft tissue infection, abscess or osteomyelitis, or puerperal fever related to infection by *Staphylococcus aureus*, coagulase-positive staphylococci (i.e., *S. epidermidis, S. hemolyticus,* etc.), *Streptococcus pyogenes, Streptococcus agalactiae,* Streptococcal groups C-F (minute-colony streptococci), viridans streptococci, *Corynebacterium minutissimum, Clostridium spp.,* or *Bartonella henselae*; uncomplicated acute urinary tract infection related to infection by *Staphylococcus saprophyticus* or *Enterococcus spp.*; urethritis, or cervicitis; a sexually transmitted disease related to infection by *Chiamydia trachomatis, Haemophilus ducreyi, Treponema pallidum, Ureaplasma urealyticum,* or *Neiserria gonorrheae*; toxin disease related to infection by *S. aureus* (food poisoning or toxic shock syndrome), or Groups A, B, and *C streptococci*; ulcer related to infection by Helicobacter pylori; systemic febrile syndrome related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria spp.*; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium spp.*; odontogenic infection related to infection by viridans streptococci; persistent cough related to infection by *Bordetella pertussis*; gas gangrene related to infection by *Clostridium perfringens* or Bacteroides spp.; atherosclerosis or cardiovascular disease related to infection by *Helicobacter pylori* or *Chlamydia pneumoniae*; bovine respiratory disease related to infection by *P. haemolytica, P. multocida, Mycoplasma bovis,* or *Bordetella spp.*; cow enteric disease related to infection by *E. coli* or protozoa; dairy cow mastitis related to infection by *Staph. aureus, Strep. uberis, Strep. agalactiae, Strep. dysgalactiae, Klebsiella spp., Corynebacterium,* or *Enterococcus spp.*; swine respiratory disease related to infection by *A. pleuro., P. multocida,* or *Mycoplasma spp.*; swine enteric disease related to infection by *E. coli, Lawsonia intracellularis,* Salmonella, or *Serpulina hyodysinteriae*; cow footrot related to infection by Fusobacterium spp.; cow metritis related to infection by *E. coli*, cow hairy warts related to infection by *Fusobacterium necrophorum* or *Bacteroides nodosus*; cow pinkeye related to infection by *Moraxella bovis*; cow premature abortion related to infection by protozoa; urinary tract infection in a dog or cat related to infection by *E. coli*; skin or soft tissue infection in a dog or cat related to infection by *Staph. epidermidis, Staph. intermedius, coagulase neg. Staph.* or *P. multocida*; or dental or mouth infection in a dog or cat related to infection by *Aicaligenes spp., Bacteroides spp., Clostridium spp., Enterobacter spp.,* Eubacterium, Peptostreptococcus, Porphyromonas, or Prevotella.

7. A method of treating a disorder selected from a bacterial infection, a protozoal infection, and a disorder related to a bacterial infection or protozoal infection in a mammal, fish, or bird which comprises administering to said mammal, fish or bird a therapeutically effective amount of a compound of claim 1.

8. The method of claim 7 wherein said disorder is
pneumonia, otitis media, sinusitus, bronchitis, tonsillitis, or mastoiditis related to infection by *Streptococcus pneumoniae, Haemophilus influenzae, Moraxella catarthalis, Staphylococcus aureus,* or *Peptostreptococcus spp.*; pharyngitis, rheumatic fever, or glomerulonephritis related to infection by *Streptococcus pyogenes*, Groups C and G streptococci, *Clostridium diptheriae,* or *Actinobacillus haemolyticum*; a respiratory tract infections related to infection by *Mycoplasma pneumoniae, Legionella pneumophila, Streptococcus pneumoniae, Haemophilus influenzae,* or *Chiamydia* pneumoniae; uncomplicated skin or soft tissue infection, abscess or osteomyelitis, or puerperal fever related to infection by *Staphylococcus aureus*, coagulase-posifive staphylococci (i.e., *S. epidernidis, S. hemolyticus*, etc.), *Streptococcus pyogenes, Streptococcus agalactiae*, Streptococcal groups C-F (minute-colony streptococci), viridans streptococci, *Corynebacterium minutissimum, Clostridium spp.*, or *Bartonella henselae*; uncomplicated acute urinary tract infection related to infection by *Staphylococcus saprophyticus* or *Enterococcus spp.*; urethritis, or cervicifis; a sexually transmitted disease related to infection by *Chlamydia trachomatfs, Haemophilus ducreyi, Treponema pallidum, Ureaplasma urealyticum*, or *Neiserria gonorrheae*; toxin disease related to infection by *S. aureus* (food poisoning or toxic shock syndrome), or Groups A, B, and C streptococci; ulcer related to infection by Helicobacter pyloh, systemic febrile syndrome related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria spp.*; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium spp.*; odontogenic infection related to infection by viridans streptococci; persistent cough related to infection by *Bordetella pertussis*; gas gangrene related to infection by *Clostridium perfringens* or *Bacteroides spp.*; atherosclerosis or cardiovascular disease related to infection by *Helicobacter pylori* or *Chiamydia pneumoniae*; bovine respiratory disease related to infection by *P. haemolytica, P. multocida, Mycoplasma bovis*, or *Bordetella spp.*; cow enteric disease related to infection by *E. coli* or protozoa; dairy cow mastitis related to infection by *Staph. aureus, Strep. uberis, Strep. agalactiae, Strep. dysgalactiae, Kiebsiella spp., Corynebacterium*, or *Enterococcus spp.*; swine respiratory disease related to infection by *A. pleuro., P. multocida*, or *Mycoplasma spp.*; swine enteric disease related to infection by *E. coli, Lawsonia intracellularis*, Salmonella, or *Serpulina hyodysinteriae*; cow footrot related to infection by Fusobactedum spp.; cow metritis related to infection by *E. coll*; cow hairy warts related to infection by *Fusobacterium necrophorum* or *Bacteroides nodosus*; cow pink-eye related to infection by *Moraxella bovis*; cow premature abortion related to infection by protozoa; urinary tract infection in a dog or cat related to infection by *E coli*; skin or soft tissue infection in a dog or cat related to infection by *Staph. epidermidis, Staph. intermedius*, coagulase neg. Staph. or *P. multocida*; or dental or mouth infection in a dog or cat related to infection by *Alcaligenes spp., Bacteroides spp., Clostridium spp., Enterobacter spp.*, Eubacterium, Peptostreptococcus, Porphyromonas, or Prevotella.

9. A pharmaceutical compositon for the treatment of non-small ccll lung cancer in a mammal which comprises a therapeutically effective amount of a compound of claim 1 and a pharmaceutically acceptable carrier.

10. A method of treating non-small cell lung cancer in a mammal which comprises administering to said mammal a therapeutically effective amount of a compound of claim 1.

* * * * *